(12) United States Patent
Maiberg

(10) Patent No.: US 12,427,293 B2
(45) Date of Patent: Sep. 30, 2025

(54) LUNG TREATMENT

(71) Applicant: Skybeam Limited, Nicosia (CY)

(72) Inventor: Eduard Maiberg, Jerusalem (IL)

(73) Assignee: Skybeam Limited, Nicosia (CY)

( * ) Notice: Subject to any disclaimer, the term of this patent is extended or adjusted under 35 U.S.C. 154(b) by 0 days.

(21) Appl. No.: 19/101,262

(22) PCT Filed: Aug. 4, 2023

(86) PCT No.: PCT/IB2023/057900
§ 371 (c)(1),
(2) Date: Feb. 5, 2025

(87) PCT Pub. No.: WO2024/028825
PCT Pub. Date: Feb. 8, 2024

(65) Prior Publication Data
US 2025/0256083 A1    Aug. 14, 2025

Related U.S. Application Data

(60) Provisional application No. 63/395,380, filed on Aug. 5, 2022.

(51) Int. Cl.
*A61M 37/00* (2006.01)
*A61B 1/00* (2006.01)
(Continued)

(52) U.S. Cl.
CPC ..... *A61M 37/0092* (2013.01); *A61B 1/00082* (2013.01); *A61B 1/00087* (2013.01); *A61B 1/05* (2013.01); *A61B 1/2676* (2013.01); *A61N 1/0519* (2013.01); *A61N 1/325* (2013.01); *A61M 2025/105* (2013.01);
(Continued)

(58) Field of Classification Search
CPC ....... A61B 34/20; A61B 90/361; A61B 90/37; A61B 2018/00285; A61B 2018/00541; A61B 2018/00666; A61B 2018/00702; A61B 2018/00714; A61B 2018/00791;
(Continued)

(56) References Cited

U.S. PATENT DOCUMENTS 5,158,536 A    10/1992    Sekins et al.
6,004,269 A    12/1999    Crowley et al.
(Continued)

FOREIGN PATENT DOCUMENTS

WO    WO 2024/028825    2/2024

OTHER PUBLICATIONS

International Search Report and the Written Opinion Dated Nov. 24, 2023 From the International Searching Authority Re. Application No. PCT/IB2023/057900. (17 Pages).
(Continued)

*Primary Examiner* — Deanna K Hall

(57) ABSTRACT

The invention relates to methods and system for locally treating a wound (for example, ARDS) of a lung tissue, or mediastinum condition, comprising choosing a target in said tissue requiring treatment; insertion trans-bronchial catheter with mini-ultrasonic therapeutic transducers as close as possible to the target; calibrating contact, calibrating position and irradiating said target with therapeutic ultrasonic waves. Optionally, also providing treatment using phonophoresis and iontophoresis for local administration of drugs into the wound.

12 Claims, 11 Drawing Sheets

(51) Int. Cl.
*A61B 1/05* (2006.01)
*A61B 1/267* (2006.01)
*A61N 1/05* (2006.01)
*A61N 1/32* (2006.01)
*A61M 25/10* (2013.01)
*A61N 7/00* (2006.01)

(52) U.S. Cl.
CPC ............... *A61M 2025/1086* (2013.01); *A61M 2210/1035* (2013.01); *A61N 2007/0017* (2013.01); *A61N 2007/0043* (2013.01)

(58) Field of Classification Search
CPC ...... A61M 37/0092; A61M 2037/0007; A61N 1/32; A61N 1/325; A61N 7/022
See application file for complete search history.

(56) References Cited

U.S. PATENT DOCUMENTS

| | | | |
|---|---|---|---|
| 10,524,859 | B2 | 1/2020 | Vrba et al. |
| 11,020,618 | B1 | 6/2021 | Warnking |
| 2003/0018270 | A1 | 1/2003 | Makin et al. |
| 2006/0161233 | A1 | 7/2006 | Barry et al. |
| 2014/0058294 | A1 | 2/2014 | Gross et al. |
| 2016/0184570 | A1 | 6/2016 | Grace et al. |
| 2016/0375235 | A1 | 12/2016 | Schoenle et al. |
| 2021/0308450 | A1 | 10/2021 | Gruba et al. |

OTHER PUBLICATIONS

Balamugesh et al. "Endobronchial Ultrasound: A New Innovation in Bronchoscopy", Lung India, 26(1): 17-21, Jan.-Mar. 2009.

Donghi et al. "Pushing the Boundaries: Transesophageal Endoscopic Ultrasound-Guided Fine-Needle Aspiration for the Diagnosis of Intraparenchymal Pulmonary Micronodules", Shanghai Chest, 4: 11-1-11-3, Apr. 10, 2020.

Gargani "Lung Ultrasound: A New Tool for the Cardiologist", Cardiovascular Ultrasound, 9(1): 6-1-6-9, Feb. 27, 2011.

Khan et al. "The Role of EkoSonic Endovascular System or EKOS® in Pulmonary Embolism", Cureus, 11(12): e6380-1 e6380-8, Dec. 14, 2019.

Liu et al. "Endobronchial High-Intensity Ultrasound for Thermal Therapy of Pulmonary Malignancies: Simulations With Patient-Specific Lung Models", International Journal of Hyperthermia, 36(1): 1107-1120, Published Online Nov. 14, 2019.

International Preliminary Report on Patentability Dated Feb. 20, 2025 From the International Bureau of WIPO Re. Application No. PCT/IB2023/057900 (10 Pages).

LUNG TREATMENT

RELATED APPLICATIONS

This application is a National Phase of PCT Patent Application No. PCT/IB2023/057900 having International filing date of Aug. 4, 2023, which claims the benefit of priority under 35 USC § 119(e) of U.S. Provisional Patent Application No. 63/395,380 filed on Aug. 5, 2022. The contents of the above applications are all incorporated by reference as if fully set forth herein in their entirety.

FIELD AND BACKGROUND OF THE INVENTION

The present invention, in some embodiments thereof, relates to system and methods for local lung treatment and, more particularly, but not exclusively, to trans-bronchial therapeutic ultrasound—system and methods, for example for the treatment for ARDS, and thromboembolic complication of mediastinum (mediastinum condition).

Local, non-invasive treatment of pulmonary tissue lesions, from inflammatory processes to ARDS, including oncological pathologies, are still very relevant and practically unresolved issues.

Additionally, a potential advantage of performing therapeutic ultrasound is the ability to mechanically cleanse the wound, accelerate angiogenesis and angiokinesis, as well as accelerating tissue regeneration processes, which fulfils necessary criteria for the local treatment of a wide variety of tissues, from diabetic leg to reproductive organs.

For many years, the lung has been considered off-limits for ultrasound. Features of the anatomical structure of the lungs, namely the presence of air in the pulmonary alveoli, which fully reflects ultrasonic waves, as well as an almost impassable ultrasound rib-muscular corset of the chest in which the lungs are located, make this organ practically impossible for the use of external therapeutic ultrasound.

However, it has been recently shown that lung diagnostic ultrasound (LUS) may represent a useful tool for the evaluation of many pulmonary conditions, as mentioned in the review written by Laura Gargani, titled "Lung ultrasound: a new tool for the cardiologist". With ultrasound the clearest diagnostic vs. therapeutic definition would be that diagnostic ultrasound is used to assess medical conditions whereas therapeutic ultrasound is used to treat them.

Additional background art for diagnostic ultrasound includes U.S. Pat. No. 8,961,508 disclosing systems, assemblies, and methods to treat pulmonary diseases used to decrease nervous system input to distal regions of the bronchial tree within the lungs. Treatment systems damage nerve tissue to temporarily or permanently decrease nervous system input. The treatment systems are capable of heating nerve tissue, cooling the nerve tissue, delivering a flowable substance that cause trauma to the nerve tissue, puncturing the nerve tissue, tearing the nerve tissue, cutting the nerve tissue, applying pressure to the nerve tissue, applying ultrasound to the nerve tissue, applying ionizing radiation to the nerve tissue, disrupting cell membranes of nerve tissue with electrical energy, or delivering long acting nerve blocking chemicals to the nerve tissue.

U.S. Pat. No. 10,307,580B2 disclosing methods, devices and systems adapted for applying drugs or therapeutic agents to biological conduits, e.g., vascular lumens. More specifically, it discloses enhancing the uptake of drugs or therapeutic agents encapsulated in microbubbles in combination with ultrasound energy as well as applying drugs or therapeutic agents in a cyclic manner using a pulse generator that may be matched in frequency with a patient's blood pulsing.

U.S. Pat. No. 20,180,193,078A1 disclosing systems, methods and devices for the treatment of tissue. A system includes an elongate tube with a distal portion. A treatment element is positioned on the elongate tube distal portion, the treatment element constructed and arranged to treat target tissue.

A scientific article by Liu et al, "Endobronchial high-intensity ultrasound for thermal therapy of pulmonary malignancies: simulations with patient-specific lung models", disclosing study for the feasibility of endobronchial ultrasound applicators for thermal ablation of lung tumors using acoustic and biothermal simulations. The study showed that simulations demonstrated the feasibility of endobronchial ultrasound applicators to deliver thermal coagulation of 2-3 cm diameter tumors adjacent to or accessible from major and deep lung airways.

A scientific article by Bakamugesh et al, "*Endobronchial ultrasound: A new innovation in bronchoscopy*", disclosing the use of an EBUS mini-probe for analyzing the multilayered structure of the tracheobronchial wall and for performing biopsies of peripheral lesions.

A scientific article by Donghi et al, "*Pushing the boundaries: transesophageal endoscopic ultrasound-guided fine-needle aspiration for the diagnosis of intraparenchymal pulmonary micronodules*", disclosing the use of Endobronchial ultrasonography (EBUS) videobronchoscope for transesophageal exploration (EUS-B-FNA).

Thus, until now, for lung, exclusively diagnostic ultrasound has been used.

Treatment of thromboembolic complications of mediastinum, especially pulmonary embolism, is still associated with high mortality. The most progressive technique for today is the introduction of a catheter with an ultrasonic sensor into the pulmonary artery with the parallel administration of thrombolytics, as shown in the article written by Khan et al, titled "The Role of EkoSonic Endovascular System or EKOS® in Pulmonary Embolism". It should be noted that despite the high invasiveness of this procedure, it has become a state of the art for many categories of patients.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A catheter system for treating a wound, comprising:
  a. at least one catheter comprising proximal end and a distal end; said distal end comprising:
     i. one or more ultrasonic transmitters;
     ii. an inflatable balloon covering said one or more ultrasonic transmitters; said inflatable balloon comprising a first electrode located at a proximal location of said inflatable balloon and a second electrode located at a distal location of said inflatable balloon;
     iii. a plurality of a first type of openings located on a surface of said balloon; said location of said first type of openings being co-located to a location of said one or more ultrasonic transmitters on said catheter;

iv. a plurality of a second type of openings located on a surface of said balloon; said location of said second type of openings being co-located to a location of said first electrode.

Example 2. The catheter system according to example 1, further comprising at least one liquid configured to inflate said inflatable balloon.

Example 3. The catheter system according to example 2, wherein said at least one liquid comprises at least one drug.

Example 4. The catheter system according to example 2, wherein said at least one liquid is saline.

Example 5. The catheter system according to any one of examples 1-4, further comprising one or more controls located at said proximal end of said catheter device and configured to control a movement of said distal end of said catheter device.

Example 6. The catheter system according to any one of examples 1-5, further comprising a video camera located at most distal end of said catheter device.

Example 7. The catheter system according to any one of examples 1-6, wherein said at least one catheter is configured to provide phonophoresis treatment.

Example 8. The catheter system according to any one of examples 1-6, wherein said at least one catheter is configured to provide iontophoresis treatment.

Example 9. The catheter system according to any one of examples 1-8, further comprising an external unit to which said at least one catheter is connected, said external unit comprising:
  a. a video unit comprising a navigation system, configured for manipulating said at least one catheter and provide visualization means from said video camera to a user;
  b. an electric field unit configured for generating an interference field;
  c. an ultrasonic unit configured to generate ultrasonic waves from about 0.5 MHZ to about 3 MHz, with a power up to 2 watts per cm2;
  d. a calibration unit configured for specifying a attenuation coefficient in different locations and further configured for determining the optimal localization of said one or more ultrasonic transmitters;
  e. a pressure unit configured for maintaining and monitoring a pressure in said balloon;
  f. a phonophoresis pharmaceutical unit configured for monitoring and administering said at least one drug during phonophoresis treatment;
  g. a iontophoresis pharmaceutical unit configured for monitoring and administering said at least one drug during iontophoresis treatment.

Example 10. The catheter system according to example 9, wherein said electric field unit is configured to provide current to a first catheter at a first frequency and to provide current to a second catheter at a second frequency.

Example 11. The catheter system according to example 10, wherein said first frequency is of about 4000 Hz and said second frequency is from about 4100 Hz to about 4500 Hz.

Example 12. The catheter system according to example 9, wherein said electric field unit is configured to provide electrical current which does not exceed 13 milliamps.

Example 13. A method for treating pulmonary tissue conditions, pulmonary emboli and/or thromboembolic condition of mediastinum, comprising:
  a. choosing a target in said tissue requiring treatment;
  b. advancing at least one catheter device according to example 1, towards a location in a vicinity of said target;
  c. performing contact calibration;
  d. performing location calibration;
  e. providing ultrasonic treatment.

Example 14. The method according to example 13, wherein said performing contact calibration comprises:
  a. inflating said inflatable balloon;
  b. receiving a signal from said first electrode and said second electrode;
  c. stopping inflating said balloon.

Example 15. The method according to example 13 or example 14, wherein said performing location calibration comprises:
  a. delivering a first amount of ultrasonic energy;
  b. determining a coefficient of attenuation;
  c. assessing, according to a result of said determining, whether said location in the vicinity of said target is an optimal location.

Example 16. The method according to example 15, wherein said optimal location is a location where said coefficient of attenuation is a low coefficient of attenuation.

Example 17. The method according to example 16, wherein said low coefficient of attenuation is of about 0.18 dB/mHz*cm.

Example 18. The method according to any one of examples 13-17, further comprising relocating said catheter device towards a new location in a vicinity of said target if said location calibration fails.

Example 19. The method according to any one of examples 13-17, wherein said providing ultrasonic treatment comprises irradiating said target with ultrasonic waves, said irradiating characterized by a time, force, and a number of radiation fields.

Example 20. The method according to example 19, wherein said irradiating is characterized in order to obtain a maximum therapeutic effect with minimal side effects and/or avoiding inducing cell death in said target.

Example 21. The method according to example 19, wherein said irradiating comprises irradiating at a force between about 1 MHz and about 3 MHz.

Example 22. The method according to example 19, wherein said irradiating comprises irradiating for a period of time of from about 10 sec to about 15 min.

Example 23. The method according to example 19, wherein said irradiating comprises irradiating utilizing a focused beam.

Example 24. The method according to any one of examples 13-23, further comprising monitoring a temperature of said target being treated.

Example 25. The method according to any one of examples 13-24, further comprising avoiding raising a temperature of said target being treated above a predetermined temperature.

Example 26. The method according to example 25, wherein said predetermined temperature is from about 40 degrees Celsius and about 45 degrees Celsius.

Example 27. The method according to any one of examples 13-26, further comprising actively controlling a temperature of said target being treated.

Example 28. The method according to example 27, wherein said controlling comprises changing said temperature of said target being treated.

Example 29. The method according to example 27, wherein said controlling comprises flowing cold liquids into said target when said target reaches a predetermined temperature.

Example 30. The method according to any one of examples 13-29, further comprising visually monitoring said target tissue.

Example 31. The method according to example 19, wherein said irradiating is performed by two different catheter devices operated at a same time.

Example 32. The method according to any one of examples 13-31, further comprising providing phonophoresis treatment.

Example 33. The method according to example 32, wherein said providing phonophoresis treatment comprises further inflating said inflatable balloon to a second inflation state; said second inflation state causing said plurality of first type of openings to open.

Example 34. The method according to example 32, wherein said providing phonophoresis treatment comprises delivering at least one drug while said providing phonophoresis treatment.

Example 35. The method according to any one of examples 13-34, further comprising providing iontophoresis treatment.

Example 36. The method according to example 35, wherein said providing iontophoresis treatment comprises further inflating said inflatable balloon to a third inflation state; said third inflation state causing said plurality of second type of openings to open.

Example 37. The method according to example 35, wherein said providing iontophoresis treatment comprises delivering at least one drug while said providing iontophoresis treatment.

Example 38. The method according to any one of examples 13-37, further comprising generating an interferential current by activating two distinct catheter devices towards said location.

Example 39. The method according to any one of examples 13-38, wherein said treatment is used for the treatment of one or more of ARDS, pulmonary parenchyma and mediastinal conditions.

Example 40. The method according to any one of examples 13-39, wherein said advancing is performed via esophagus and/or via trachea.

Example 1a. A method for treating a wound in a tissue in a lung, comprising:
 a. choosing a target in said tissue requiring treatment;
 b. advancing a catheter which has an ultrasonic transducer at a distal end of said catheter towards said target;
 irradiating said target with ultrasonic waves, said irradiating characterized by a time and force configured to avoid inducing cell death in said target.

Example 2a. The method according to example 1a, wherein said irradiating comprises irradiating at a force between about 1 MHz and about 3 MHz.

Example 3a. The method according to example 1a or example 2a, wherein said irradiating comprises irradiating for a period of time of from about 10 sec to about 15 min.

Example 4a. The method according to any one of examples 1a-3a, wherein said irradiating comprises irradiating utilizing a focused beam.

Example 5a. The method according to any one of examples 1a-4a, further comprising monitoring a temperature of said target being treated.

Example 6a. The method according to any one of examples 1a-5a, further comprising avoiding raising a temperature of said target being treated above a predetermined temperature.

Example 7a. The method according to example 6a, wherein said predetermined temperature is from about 40 degrees Celsius and about 45 degrees Celsius.

Example 8a. The method according to any one of examples 1a-7a, further comprising actively controlling a temperature of said target being treated.

Example 9a. The method according to example 8a, wherein said controlling comprises changing said temperature of said target being treated.

Example 10a. The method according to example 8a, wherein said controlling comprises flowing cold liquids into said target when said target reaches a predetermined temperature.

Example 11a. The method according to any one of examples 1a-10a, further comprising visually monitoring said target tissue.

Example 12a. The method according to any one of examples 1a-11a, further comprising actively seeking new targets while performing said irradiating.

Example 13a. The method according to example 12a, wherein said seeking and said irradiating are performed by a same device.

Example 14a. The method according to example 12a, wherein said seeking is performed by a diagnostic ultrasound device introduced through an additional catheter, said diagnostic ultrasound device configured for transmitting coordinates to a therapeutic ultrasound device.

Example 15a. The method according to example 12a, wherein said seeking and said irradiating are performed at the same time.

Example 16a. The method according to example 12a, wherein said seeking and said irradiating are performed by two different devices.

Example 17a. The method according to any one of examples 1a-16a, further comprising irradiating said target with laser.

Example 18a. The method according to example 17a, wherein said irradiating with laser is performed at different times than said irradiating with ultrasonic waves.

Example 19a. The method according to example 17a, wherein said irradiating with laser is performed a third of the times of an overall irradiation treatment while said irradiating with ultrasonic waves is performed two thirds of the times of said overall irradiation treatment.

Example 20a. The method according to any one of examples 1a-19a, further comprising, before said irradiating, choosing one or more locations adjacent to said target from which said irradiating will be performed.

Example 21a. The method according to example 20a, further comprising dividing performance of said irradiating between said one or more locations.

Example 22a. The method according to any one of examples 1a-21a, further comprising, before said irradiating, choosing at least three locations adjacent to said target from which said irradiating will be performed.

Example 23a. The method according to example 22a, further comprising dividing performance of said irradiating between said at least three locations.

Example 24a. The method according to any one of examples 1a-23a, further comprising locally providing or more pharmaceuticals during said treatment.

Example 25a. A method of treating pulmonary embolism (PE) in a patient, comprising:
 a. choosing at least one target requiring treatment;
 b. inserting a bronchoscope into said patient and positioning a distal end of said bronchoscope as close as possible to said at least one target;
 c. inserting a catheter comprising a distal end having therapeutic ultrasound transmitter into said bronchoscope;

d. irradiating said at least one target according to a predetermined effective irradiation program.

Example 26a. The method according to example 25a, wherein said predetermined effective irradiation program comprises irradiating at a frequency from about 1 MHz to about 3 MHz.

Example 27a. The method according to example 25a or 26a, wherein said predetermined effective irradiation program comprises irradiating said target at three irradiation fields.

Example 28a. The method according to example 27a, wherein said predetermined effective irradiation program comprises irradiating at least 10 points within said three irradiation fields.

Example 29a. The method according to example 28a, wherein said predetermined effective irradiation program comprises irradiating for a duration of at least 10 sec per point.

Example 30a. The method according to any one of examples 25a-29a, wherein said predetermined effective irradiation program comprises irradiating for a total duration of at least 5 min.

Example 31a. The method according to any one of examples 25a-30a, wherein said predetermined effective irradiation program comprises irradiating so as to reach a temperature of about 42 degrees Celsius in said target.

Example 32a. The method according to any one of examples 25a-31a, wherein said choosing comprises localization and visualization of the affected area.

Example 33a. The method according to any one of examples 25a-32a, wherein said irradiating comprises irradiating for a period of time of from about 10 sec to about 15 min.

Example 34a. The method according to any one of examples 25a-33a, wherein said irradiating comprises irradiating utilizing a focused beam.

Example 35a. The method according to any one of examples 25a-34a, further comprising monitoring a temperature of said target being treated.

Example 36a. The method according to any one of examples 25a-35a, further comprising avoiding raising a temperature of said target being treated above a predetermined temperature.

Example 37a. The method according to example 36a, wherein said predetermined temperature is from about 40 degrees Celsius and about 45 degrees Celsius.

Example 38a. The method according to any one of examples 25a-37a, further comprising actively controlling a temperature of said target being treated.

Example 39a. The method according to example 38a, wherein said controlling comprises changing said temperature of said target being treated.

Example 40a. The method according to example 38a, wherein said controlling comprises flowing cold liquids into said target when said target reaches a predetermined temperature.

Example 41a. The method according to any one of examples 25a-40a, further comprising visually monitoring said target tissue.

Example 42a. The method according to any one of examples 25a-41a, further comprising actively seeking new targets while performing said irradiating.

Example 43a. The method according to example 42a, wherein said seeking and said irradiating are performed by a same device.

Example 44a. The method according to example 42a, wherein said seeking is performed by a diagnostic ultrasound device introduced through an additional catheter, said diagnostic ultrasound device configured for transmitting coordinates to a therapeutic ultrasound device.

Example 45a. The method according to example 42a, wherein said seeking and said irradiating are performed at the same time.

Example 46a. The method according to example 42a, wherein said seeking and said irradiating are performed by two different devices.

Example 47a. The method according to any one of examples 25a-46a, further comprising irradiating said target with laser.

Example 48a. The method according to example 47a, wherein said irradiating with laser is performed at different times than said irradiating with ultrasonic waves.

Example 49a. The method according to example 47a, wherein said irradiating with laser is performed a third of the times of an overall irradiation treatment while said irradiating with ultrasonic waves is performed two thirds of the times of said overall irradiation treatment.

Example 50a. The method according to any one of examples 25a-49a, further comprising, before said irradiating, choosing one or more locations adjacent to said target from which said irradiating will be performed.

Example 51a. The method according to example 50a, further comprising dividing performance of said irradiating between said one or more locations.

Example 52a. The method according to any one of examples 25a-51a, further comprising, before said irradiating, choosing at least three locations adjacent to said target from which said irradiating will be performed.

Example 53a. The method according to example 52a, further comprising dividing performance of said irradiating between said at least three locations.

Example 54a. The method according to any one of examples 25a-53a, further comprising locally providing or more pharmaceuticals during said treatment.

Example 55a. A method for treating pulmonary parenchyma and mediastinal conditions in a patient, the method comprising:
  a. choosing at least one target requiring treatment;
  b. inserting a bronchoscope or gastroscope into the esophagus or stomach of said patient and positioning a distal end of said bronchoscope as close as possible to said at least one target;
  c. inserting a catheter comprising a distal end having therapeutic ultrasound transmitter into said bronchoscope;
  d. irradiating said at least one target according to a predetermined maximum irradiation program.

Example 56a. The method according to example 55a, wherein said predetermined maximum irradiation program comprises irradiating at a frequency from about 5 MHz to about 50 MHz.

Example 57a. The method according to example 55a or 56a, wherein said predetermined maximum irradiation program comprises irradiating said target at five irradiation fields.

Example 58a. The method according to example 57a, wherein said predetermined maximum irradiation program comprises irradiating at least 20 points within said three irradiation fields.

Example 59a. The method according to example 58a, wherein said predetermined maximum irradiation program comprises irradiating for a duration of at least 30 sec per point.

Example 60a. The method according to any one of examples 55a-59a, wherein said predetermined maximum irradiation program comprises irradiating for a total duration of at least 30 min.

Example 61a. The method according to any one of examples 55a-60a, wherein said predetermined maximum irradiation program comprises irradiating so as to reach a temperature of about 45 degrees Celsius in said target.

Example 62a. The method according to any one of examples 55a-61a, wherein said choosing comprises localization and visualization of the affected area.

Example 63a. The method according to any one of examples 55a-62a, wherein said irradiating comprises irradiating for a period of time of from about 10 sec to about 15 min.

Example 64a. The method according to any one of examples 55a-63a, wherein said irradiating comprises irradiating utilizing a focused beam.

Example 65a. The method according to any one of examples 55a-64a, further comprising monitoring a temperature of said target being treated.

Example 66a. The method according to any one of examples 55a-65a, further comprising avoiding raising a temperature of said target being treated above a predetermined temperature.

Example 67a. The method according to example 66a, wherein said predetermined temperature is from about 40 degrees Celsius and about 45 degrees Celsius.

Example 68a. The method according to any one of examples 55a-67a, further comprising actively controlling a temperature of said target being treated.

Example 69a. The method according to example 68a, wherein said controlling comprises changing said temperature of said target being treated.

Example 70a. The method according to example 68a, wherein said controlling comprises flowing cold liquids into said target when said target reaches a predetermined temperature.

Example 71a. The method according to any one of examples 55a-70a, further comprising visually monitoring said target tissue.

Example 72a. The method according to any one of examples 55a-71a, further comprising actively seeking new targets while performing said irradiating.

Example 73a. The method according to example 72a, wherein said seeking and said irradiating are performed by a same device.

Example 74a. The method according to example 72a, wherein said seeking is performed by a diagnostic ultrasound device introduced through an additional catheter, said diagnostic ultrasound device configured for transmitting coordinates to a therapeutic ultrasound device.

Example 75a. The method according to example 72a, wherein said seeking and said irradiating are performed at the same time.

Example 76a. The method according to example 72a, wherein said seeking and said irradiating are performed by two different devices.

Example 77a. The method according to any one of examples 55a-76a, further comprising irradiating said target with laser.

Example 78a. The method according to example 77a, wherein said irradiating with laser is performed at different times than said irradiating with ultrasonic waves.

Example 79a. The method according to example 77a, wherein said irradiating with laser is performed a third of the times of an overall irradiation treatment while said irradiating with ultrasonic waves is performed two thirds of the times of said overall irradiation treatment.

Example 80a. The method according to any one of examples 55a-79a, further comprising, before said irradiating, choosing one or more locations adjacent to said target from which said irradiating will be performed.

Example 81a. The method according to example 80, further comprising dividing performance of said irradiating between said one or more locations.

Example 82a. The method according to any one of examples 55a-81a, further comprising, before said irradiating, choosing at least three locations adjacent to said target from which said irradiating will be performed.

Example 83a. The method according to example 82a, further comprising dividing performance of said irradiating between said at least three locations.

Example 84a. The method according to any one of examples 55-83a, further comprising locally providing or more pharmaceuticals during said treatment.

Example 85a. The method according to example 55a, wherein said choosing comprises localization and visualization of the affected area.

Example 86a. A method of treating a wound in a tissue of a lung and/or parenchyma in a patient, the method comprising:
  a. choosing at least one target in said tissue requiring treatment;
  b. introducing into said patient a bronchoscope and positioning said bronchoscope in the vicinity of said target;
c. inserting a catheter comprising a distal end having therapeutic ultrasound transmitter into said bronchoscope;
d. irradiating said at least one target according to a predetermined efficient mode program.

Example 87a. The method according to example 86a, wherein said predetermined efficient mode program comprises irradiating at a frequency from about 1 MHz to about 3 MHz.

Example 88a. The method according to example 86a or 87a, wherein said predetermined efficient mode program comprises irradiating said target at three irradiation fields.

Example 89a. The method according to example 88a, wherein said predetermined efficient mode program comprises irradiating at least 10 points within said three irradiation fields.

Example 90a. The method according to example 89a, wherein said predetermined efficient mode program comprises irradiating for a duration of at least 10 sec per point.

Example 91a. The method according to any one of examples 86a-90a, wherein said predetermined efficient mode program comprises irradiating for a total duration of at least 5 min.

Example 92a. The method according to any one of examples 86a-91a, wherein said predetermined efficient mode program comprises irradiating so as to reach a temperature of about 42 degrees Celsius in said target.

Example 93a. The method according to any one of examples 86a-92a, wherein said choosing comprises localization and visualization of the affected area.

Example 94a. The method according to any one of examples 86a-93a, wherein said irradiating comprises irradiating for a period of time of from about 10 sec to about 15 min.

Example 95a. The method according to any one of examples 86a-94a, wherein said irradiating comprises irradiating utilizing a focused beam.

Example 96a. The method according to any one of examples 86a-95a, further comprising monitoring a temperature of said target being treated.

Example 97a. The method according to any one of examples 86a-96a, further comprising avoiding raising a temperature of said target being treated above a predetermined temperature.

Example 98a. The method according to example 97a, wherein said predetermined temperature is from about 40 degrees Celsius and about 45 degrees Celsius.

Example 99a. The method according to any one of examples 86a-98a, further comprising actively controlling a temperature of said target being treated.

Example 100a. The method according to example 99a, wherein said controlling comprises changing said temperature of said target being treated.

Example 101a. The method according to example 99a, wherein said controlling comprises flowing cold liquids into said target when said target reaches a predetermined temperature.

Example 102a. The method according to any one of examples 86aa-101, further comprising visually monitoring said target tissue.

Example 103a. The method according to any one of examples 86a-102a, further comprising actively seeking new targets while performing said irradiating.

Example 104a. The method according to example 103a, wherein said seeking and said irradiating are performed by a same device.

Example 105a. The method according to example 103a, wherein said seeking is performed by a diagnostic ultrasound device introduced through an additional catheter, said diagnostic ultrasound device configured for transmitting coordinates to a therapeutic ultrasound device.

Example 106a. The method according to example 103a, wherein said seeking and said irradiating are performed at the same time.

Example 107a. The method according to example 103a, wherein said seeking and said irradiating are performed by two different devices.

Example 108a. The method according to any one of examples 86a-107a, further comprising irradiating said target with laser.

Example 109a. The method according to example 108a, wherein said irradiating with laser is performed at different times than said irradiating with ultrasonic waves.

Example 110a. The method according to example 108a, wherein said irradiating with laser is performed a third of the times of an overall irradiation treatment while said irradiating with ultrasonic waves is performed two thirds of the times of said overall irradiation treatment.

Example 111a. The method according to any one of examples 86a-110a, further comprising, before said irradiating, choosing one or more locations adjacent to said target from which said irradiating will be performed.

Example 112a. The method according to example 111a, further comprising dividing performance of said irradiating between said one or more locations.

Example 113a. The method according to any one of examples 86a-112a, further comprising, before said irradiating, choosing at least three locations adjacent to said target from which said irradiating will be performed.

Example 114a. The method according to example 113a, further comprising dividing performance of said irradiating between said at least three locations.

Example 115a. The method according to any one of examples 86a-114a, further comprising locally providing or more pharmaceuticals during said treatment.

Example 116a. The method according to example 115a, wherein said choosing is according to one or more of R-ray, CT, MRI and US.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as providing the right intensity of ultrasound for the tissue to be treated, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
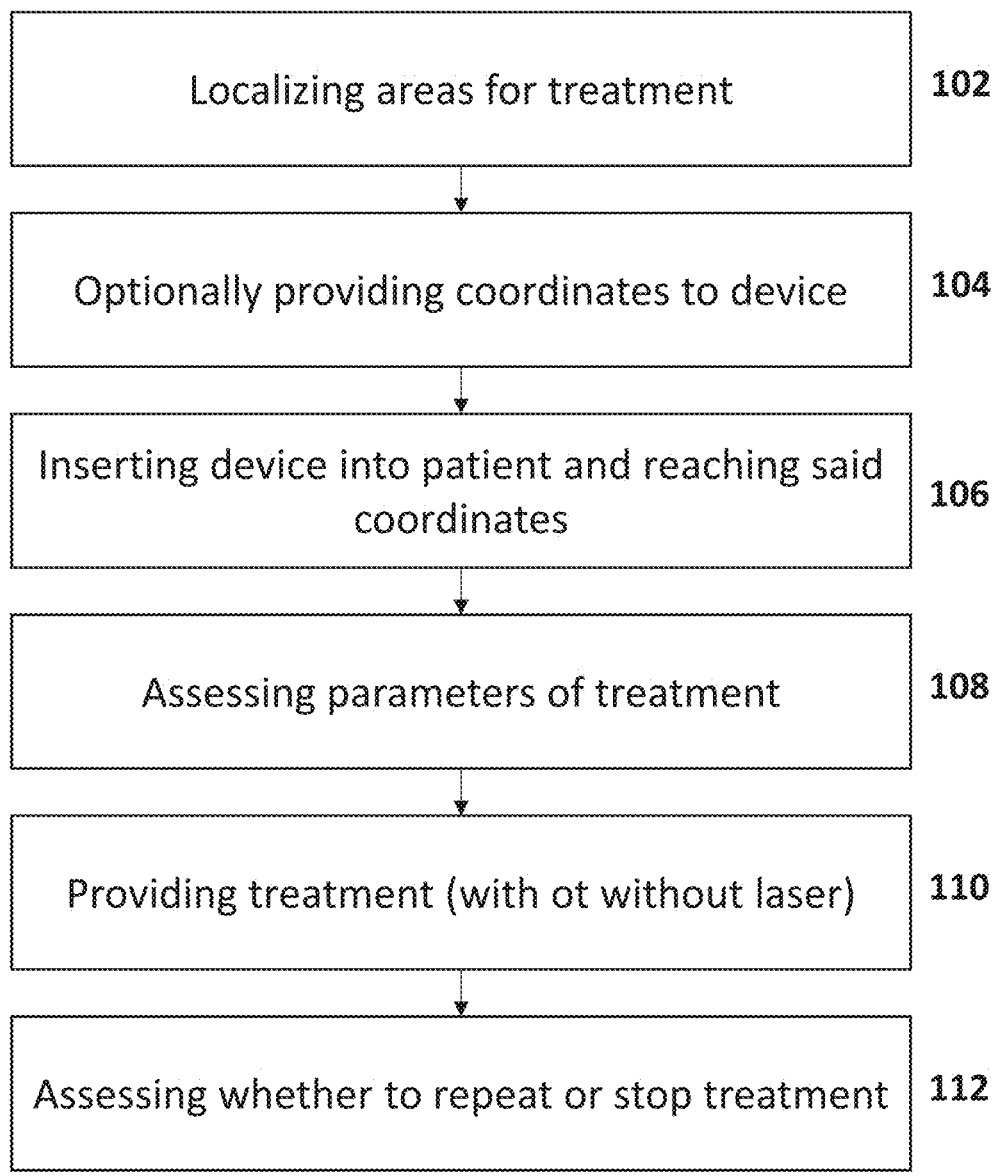
FIG. 1 is a flowchart of an exemplary treatment method, according to some embodiments of the invention.

The present invention, in some embodiments thereof, relates to system and methods for local lung treatment and, more particularly, but not exclusively, to trans-bronchial therapeutic ultrasound system and methods for local lung treatment also in patients with ARDS, and thromboembolic complication of mediastinum (mediastinum condition).

Overview

An aspects of some embodiments of the invention relates to local, non-invasive treatment of pulmonary tissue lesions from inflammatory processes to ARDS and oncological pathology. In some embodiments, therapeutic ultrasound due to its qualities, namely invasiveness, comprises the ability to mechanically cleanse the wound, accelerate angiogenesis and angiokinesis, as well as tissue regeneration processes, has all the necessary criteria for the local treatment of a wide variety of tissues, from diabetic leg to reproductive organs. More than 70% of patients with COVID 19 die from pulmonary complications. Without being bound to theory, it has been shown that the damage of the lung parenchyma in a variety of diseases is a particular type of "bed healing wounds". This is very clearly visible especially in ARDS, where the main biological markers responsible for poor wound healing behave the same way as in poorly healing wounds of a completely different etiology (pressure wounds, venous wounds, diabetic wounds). Thus, we are dealing with a poorly healing vascular wound in the lungs, which, like any wound, primarily requires local treatment. Currently, such treatment is not carried out, which explains the very high mortality rate of such patients, more than 40%. In some embodiments, the inventions relates to trans-bronchial therapeutic ultrasound (mini invasive) alone or in combination with phonophoresis/iontophoresis and, optionally, laser for local treatment of lung diseases and mediastinum conditions. In some embodiments, in order for therapeutic ultrasound to pass to the affected area in the lungs/mediastinum, a calibration is performed, which allows to determine the places as close to the lesion focus as possible, but at the same time with the least aeration and the most passable for ultrasound.

An aspect of some embodiments of the invention relates to treating a lung using ultrasound. In some embodiments, the ultrasound is delivered using a trans-bronchial therapeutic ultrasound approach, either alone or in combination with one or more of phonophoresis, iontophoresis and laser, for the local treatment of lung diseases and mediastinum conditions. In some embodiments, before applying a therapeutic amount of ultrasonic radiation, a calibration process is performed in order to assess one or more locations that fulfil of one or more of the following requirements: locations that are as close as possible to the lesions requiring treatment and locations with the least aeration and the most passable for ultrasound. In some embodiments, the calibration and positioning are performed by determining the attenuation coefficient, namely, the identification of the most passable areas for ultrasound, which are located as close as possible to the focus. In some embodiments, other methods can be used for calibration. In some embodiments, irradiating the target with ultrasonic waves is characterized by a time, force, the number of radiation fields, to obtain the maximum therapeutic effect with minimal side effects and avoid inducing cell death in said target. In some embodiments, the treatment comprises locally providing one or more pharmaceuticals during the treatment by using a special catheter Calibration Therapeutic Catheter (CTCat) with transducers covered with a balloon in which there are micro-holes in front of the transducers that open under a certain pressure in the balloon. In some embodiments, the micro-holes can pass the medicinal substance in the balloon through them. In some embodiments, at the same time, the ultrasonic wave mechanically introduces the drug into the adjacent tissues and delivers it to the lesion focus (phonophoresis). Catheters have a size range depending on their resistance and differ in Contact Pressure (minimum pressure to be created in the balloon to achieve full contact with the bronchial wall and the perforation holes remain closed. The use of contact pressure prevents overgrowth and bronchial wall ischemia (frequent complications from excessive inflating of the balloon). For example, catheter with resistance R1 has a contact pressure of 10 mm/H2O, R 2-15 mm/H2O, R3-20 mm/H2O etc. In some embodiments, the treatment method comprises providing an interferential current. In some embodiments, to do this, two medium frequency currents are used. In some embodiments, they are known as carrier waves as they do not produce muscle or nerve stimulation and are used just used to get the greater depth of penetration and to produce interferential current. In some embodiments, iontophoresis, where an electric field is used as a drug promoter, when drug ions, depending on their charge, move the drug into the tissue towards the other pole. It is based on the principle that in a given electric field, positively charged drug ions (cations) are repelled by a positive electrode (anode) and are directed to the cathode. For example, Ketoprofen being repelled by the negative electrode (cathode), follow the anode. In some embodiments, interferential current is used for iontophoresis.

An aspect of some embodiments of the invention relates to a system comprise an external unit to which one or more dedicated catheters are connected. In some embodiments, the external unit comprises all the dedicated controls to actuate all the different mechanisms of the different catheters. In some embodiments, the external unit comprises one or more of: 1. A video unit with navigation system. 2. An electric field unit configured for generating an interference field, for example, a first pair receives 4000 Hertz, while the second—from 4100 to 4500 Hertz. In some embodiments, at the same time, the current strength does not exceed 13 milliamps. 3. An ultrasonic unit configured to generate waves from 0.5 to 3 MHz with a power of up to 2 watts per cm2. In some embodiments, it also monitors the ambient temperature of the probe. In some embodiments, the ultrasonic generator generates an ultrasonic pulsed/non pulsed waveform. 4. A calibration unit, configured for specifying the attenuation coefficient in different localizations and determines the optimal localization of transducers. 5. A unit for monitoring and maintaining pressure in the balloon. 6. A unit for medicine administration and dose monitoring-used to inject drugs into the catheter and monitoring doses for phonophoresis. 7. A unit for medicine administration and dose monitoring-used to inject drugs into the catheter and monitoring doses for iontophoresis.

Example 25. A method of treating pulmonary embolism (PE) or other thromboembolic mediastinal complication in a patient, comprising:

An aspect of some embodiments of the invention relates to treating a lung using ultrasound. In some embodiments, the treatment is provided from a very short distance to the relevant tissue requiring treatment. In some embodiments, the treatment is provided from within the body, for example, from within the lungs. In some embodiments, a preliminary calibration process is performed prior to the treatment, to determine one or more areas of the lung characterized by having a high level of patency for ultrasound and/or are located as close as possible to the lesion. In some embodiments, a potential advantage of performing a preliminary calibration is that it potentially avoids delivering ultrasonic energy to areas that are aerated that will reflect the ultrasonic energy thereby not providing the proper treatment. In some embodiments, therapeutic ultrasound is delivered with or without delivering a drug and/or a medicine to the lungs at the same time. In some embodiments, the calibration process comprises choosing an optimal location for the ultrasonic probes. In some embodiments, the optimal location is characterized by being location where there is no air between the probe and the location requiring treatment. In some embodiments, the optimal location is characterized by being a location closest to the location requiring treatment. In some embodiments, the optimal location is characterized by being both a location where there is no air between the probe and the location requiring treatment and it is the location closest to the location requiring treatment. In some embodiments, the calibration process utilizes attenuation of the delivered ultrasonic energy to select the location where the probe will be positioned. In some embodiments, the preliminary calibration process comprises ensuring continuous contact between the ultrasound probe and the bronchial walls. In some embodiments, the electrode comprises a mechanism configured for assessing that both the distal end and the proximal end of the area comprising the ultrasonic transmitters is in continuous contact with the bronchial walls.

In some embodiments, the ultrasound action is configured to provide a therapeutic effect, while avoiding inducing cell death. In some embodiments, the treatment is characterized by a relatively narrow and/or focused ultrasonic beam. In some embodiments, optionally, imaging is used in concomitance with the treatment. In some embodiments, imaging is used to identify, optionally in real-time, relevant locations requiring treatment, for example, locations having increased amount of fluids, or other signs of lung tissue dysfunction. In some embodiments, a potential advantage of combining trans-bronchial diagnostics and therapeutic ultrasound is that it potentially allows greater understanding of the dynamics and effectiveness of the treatment, and potentially removes the need for an increased number of x-rays that these patients would otherwise be needed to be subjected to, and therefore reducing the radiation load on the patient.

In some embodiments, as mentioned above, during treatment, the ultrasound (US) probe is brought as close as possible to the tissue requiring treatment from within the body (intubation tube, bronchoscopy, endoscopy, laparoscopic, robotic), for example via the esophagus and/or via the trachea, for example a distance of from about 1 mm to about 1 cm; optionally, a distance from about 0.5 mm to about 3 cm; optionally a distance from about 0.1 mm to about 5 cm. In some embodiments, a potential advantage of bringing the US probe close to the tissue is that it potentially avoids the problems caused by interfering tissues, when treatment is applied from outside the body. Additionally, another potential advantage, is that it potentially allows the reduction of the treatment session time compared to external treatment, for example to a treatment session time from about 3 min to about 5 min; optionally from about 2 min to about 10 min; optionally from about 1 min to about 15 min. Additionally, another potential advantage, is that it potentially allows the use of a focused US beam, which potentially increases the specificity of the area of treatment. Additionally, another potential advantage, is that it potentially allows providing treatment to a patient, no matter it physical constitution, for example, in overweight patients, there is no possibility of using external ultrasound of thoracic origin, since penetration is almost 0 due to the bones and increased body mass.

In some embodiments, the treatment allows monitoring the change (increase or decrease) of the temperature in the lung, and more specifically in the parenchyma wound, which rises as a result of the hyperthermic effect of therapeutic ultrasound (from about 40 to about 45 Celsius), and which decreases after ceasing the treatment. In some embodiments, the ultrasound emissions are monitored and controlled so as to ensure providing a therapeutic effect while potentially avoiding cell damage. In some embodiments, a potential advantage of the system and method is that since the US probe is brought very close to the desired lung tissue, it is possible to control the temperature in the wound itself and, without side effects, positively use the hyperthermic effect of ultrasound, which potentially has a positive effect in above ranges on improving blood circulation in the lung wound; this is contrary to external ultrasound, in which only the temperature of the transducer and the skin can be monitored, while the temperature in the wound area is not controlled.

An aspect of some embodiments of the invention relates to treatment of pulmonary wounds, optionally due to COVID19 with difficult ARDS, and connected to mechanical ventilation or ECMO. In some embodiments, the treatment is a local treatment of the wound in the lungs. In some embodiments, the treatment is a local treatment provided from within the lungs and not from outside the body of the patient. In some embodiments, the treatment is treatment of the pulmonary parenchyma, vessels and alveolar-vascular complex. In some embodiments, identification of candidates for receiving the treatment comprises evaluating the levels of one or more of IL6, MMP-9, TNF-α, D-dimer, TGF-beta1, which, without connection to the wound etiology, determine the ultimate severity in the healing of lesions. In some embodiments, candidates will present one or more of the following parameters: High serum levels of IL-6; High serum levels of TNF-α; High serum levels of Matrix metalloproteinases (MMP-9); High serum levels of D-dimer (where those requiring intubation were at a higher risk of developing a pulmonary embolism (PE)); and High serum levels of TGF-β. It should be understood that these are exemplary parameters, and that the treatment could be provided to patients that do not meet these exact parameters criteria.

In some embodiments, blood/serum levels of the parameters disclosed above (one or more of IL6, MMP-9, TNF-α, D-dimer, TGF-beta1) are evaluated after and/or during the time that the treatment is provided in order to assess the level of progression of the treatment, for example, reduction in the parameters of the molecules above, in relation to the values found before beginning of the treatment, may show an improvement in the status of the lesions/wounds. In some embodiments, the monitoring of the values of one or more of IL6, MMP-9, TNF-α, D-dimer, TGF-beta1, are compared with initial values before providing the treatment. In some embodiments, the monitoring is performed after each treatment. In some embodiments, the monitoring is performed a day or two after each treatment. In some embodiments, the monitoring is performed a determined time after providing the treatment according to the medical personnel instructions.

In some embodiments, the treatment comprises therapeutic, high-frequency, low power ultrasound configured to locally treating wounds in the lungs. In some embodiments, albeit the fact that the lungs are filled with air, which does not allow to conduct ultrasound, locations in the lung that are struck with wounds and/or inflammation are affected by the therapeutic ultrasound waves, since those locations are not only filled with air, but also liquids generated due to the inflammatory processes.

In some embodiments, in order to optimize the delivery of the therapeutic ultrasound waves a therapeutic ultrasonic probe is brought closely to the focus of the lesions in the lungs, which are the bronchial trees. In some embodiments, treatment comprises the insertion of a finest catheter with therapeutic ultrasound probes, which are configured to reach almost in any site in the lungs, therefore avoiding any obstacle in the way of the ultrasonic wave to the lesion in lung tissue (except for the thin wall of the bronchi). In some embodiments, a potential advantage of dong this is that it potentially allows providing all the positive qualities of therapeutic ultrasound, which are important for local treatment of the wound (cleanse, anti-inflammatory, hyper-thermal, angiogenic and angiokinetic, and other local qualities of ultrasound in the repair processes). In some embodiments, the method is relatively not invasive and can be optionally combined with a diagnostic ultrasound, which can also be inserted transbronchially and can be used to localize the lesion of pulmonary parenchyma and can be used to transform coordinates to the therapeutic ultrasound, which can potentially allow to increase the accuracy of the positioning of the catheter with the therapeutic ultrasound. In some embodiments, the treatment comprises providing treatment without causing side effects. In some embodiments, additionally, the catheter with the therapeutic ultrasound can be used in the esophagus or stomach with the control of the endoscope and also accurately being subsequently subjected to the closest distance to the lung lesion. In some embodiments, taking into account the anti-trombotic effect of the therapeutic ultrasound, the calibration/therapeutic catheter is maintained transbronchyally or endoscopically independently or in combination with a local anticoagulant, which can treat the thromboembolic complications of the mediastinum, including pulmonary embolism. In some embodiments, a potential advantage of the treatment of the present invention is that is a much less invasive procedure for the treatment of pulmonary embolism than the cauterization of the pulmonary artery, which is carried out in EKOS. Additionally, with the treatment disclosed herein, the mechanical effect of ultrasound will manifest itself, which will bring the additional recruitment of 12-15% of the alveoli that are in a state of atelectasis and which can be open due to the micro-massage of ultrasound brought almost very close to them. Another potential advantage of the treatment method of the present invention is that it overcomes the fallbacks of the use of external ultrasound to the lung area of the chest, which cannot be effective due to the presence of bones and tissue that practically does not allow passage of the ultrasound, due to high ecogenography of bones. In addition, the penetrating capacity of the therapeutic ultrasound is about 5 cm. It would be clear to a person having skills in the art that it is practically impossible for the ultrasound waves to reach the pulmonary tissue due to the thickness of the wall of the chest and the diversity of tissues with different impedance along the way of the beam: for example skin, subcutaneous layer, fat, bone, muscles, fascia, etc.

In some embodiments, additionally, laser is used in concomitance with the therapeutic US. In some embodiments, a laser is used in same way, by inserting a laser probe with intra bronchial catheter or endoscopically and with combination of above described therapeutic ultrasound.

An aspect of some embodiments of the invention relates to a method for treating a wound in a tissue in a lung, comprising: 1. choosing a target in said tissue requiring treatment; 2. advancing one or more tracheobronchial catheters that have an ultrasound transducers at a distal end of said catheter towards said target; the advancing is performed for example via the esophagus and/or via the trachea, 3. Performing calibration and positioning, by determining the attenuation coefficient, namely, the identification of the most passable areas for ultrasound, which are located as close as possible to the focus; irradiating said target with ultrasonic waves, said irradiating characterized by a time, force and a number of radiation fields adapted to obtain a maximum therapeutic effect with minimal side effects and avoid inducing cell death in said target.

In some embodiments, additionally, the above-described method of using therapeutic ultrasound, is provided with local administration of drugs (anticoagulants, anti-inflammatory, etc.). A potential advantage is that ultrasonic waves accelerate the introduction of drugs into tissues. In some embodiments, additionally, local administration of drugs is provided using either phonophoresis and/or using iontophoresis.

Before explaining at least one embodiment of the invention in detail, it is to be understood that the invention is not necessarily limited in its application to the details of construction and the arrangement of the components and/or methods and/or by the Examples set forth in the following description and/or illustrated in the drawings and/or the Examples. The invention is capable of other embodiments or of being practiced or carried out in various ways.

In the following paragraphs, a method of treatment will be disclosed. While an exemplary lung method of treatment will be used to explain the inventive concepts of the invention, it should be understood that the same or similar methods can be performed for different locations, for example, the method scan be used for colon treatments.

Exemplary Method

Referring now to FIG. 1 showing a flowchart of an exemplary treatment method, according to some embodiments of the invention.

Figure 2:
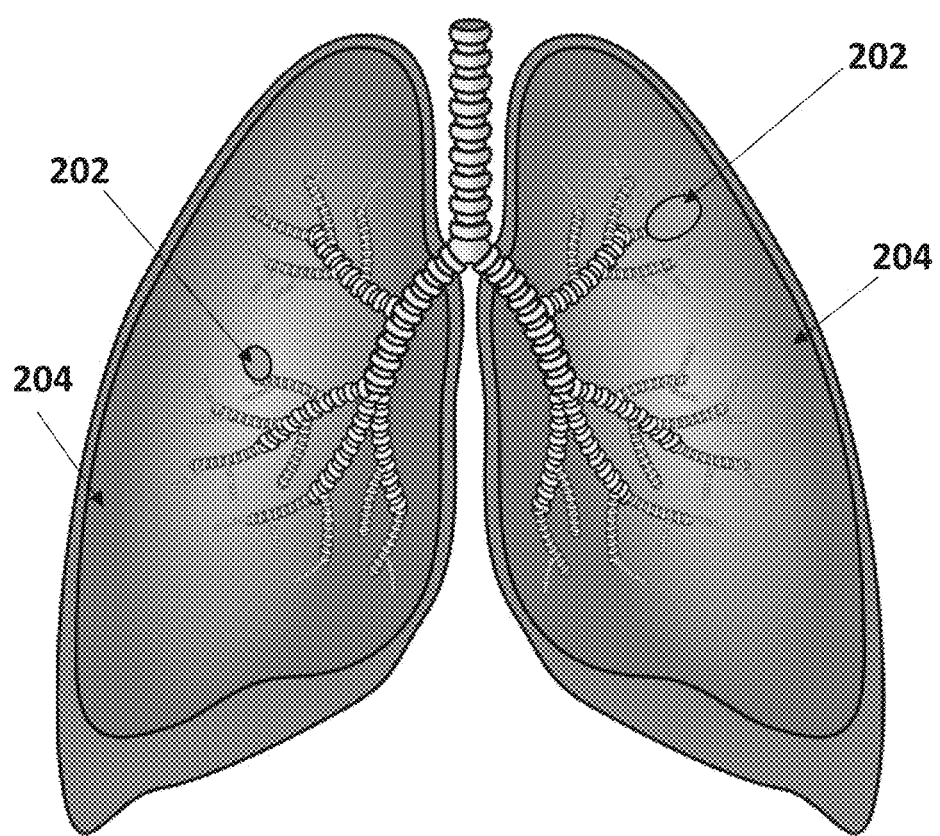
FIG. 2 is a schematic representation of localized areas of treatment, according to some embodiments of the invention.

In some embodiments, a general exemplary method of treatment comprises one or more of the following actions:

Localizing the areas of treatment 102. In some embodiments, a visual assessment of the organ in question, for example, the lung, is performed to localize the relevant areas of treatment. For example, a CT of the lungs is performed to assess the locations 202 in the lung(s) 204 that require or might require US treatment, as schematically shown in FIG. 2. In some embodiments, an US diagnostic catheter is inserted and a location and/or diagnosis of the problem is performed. In some embodiments, exemplary methods to evaluate the location in need to be treated can be X-ray, MRI, CT, and US.

Providing coordinates to device 104. In some embodiments, optionally a computerized navigational system is used to navigate the bronchoscope. Therefore, in some embodiments, the coordinates of the location within the lungs are provided to the computerized navigational system. In some embodiments, a potential advantage of using a computerized navigational system is that the navigational accuracy of such device potentially allows reaching distant and thin bronchi in the lung.

Figure 3:
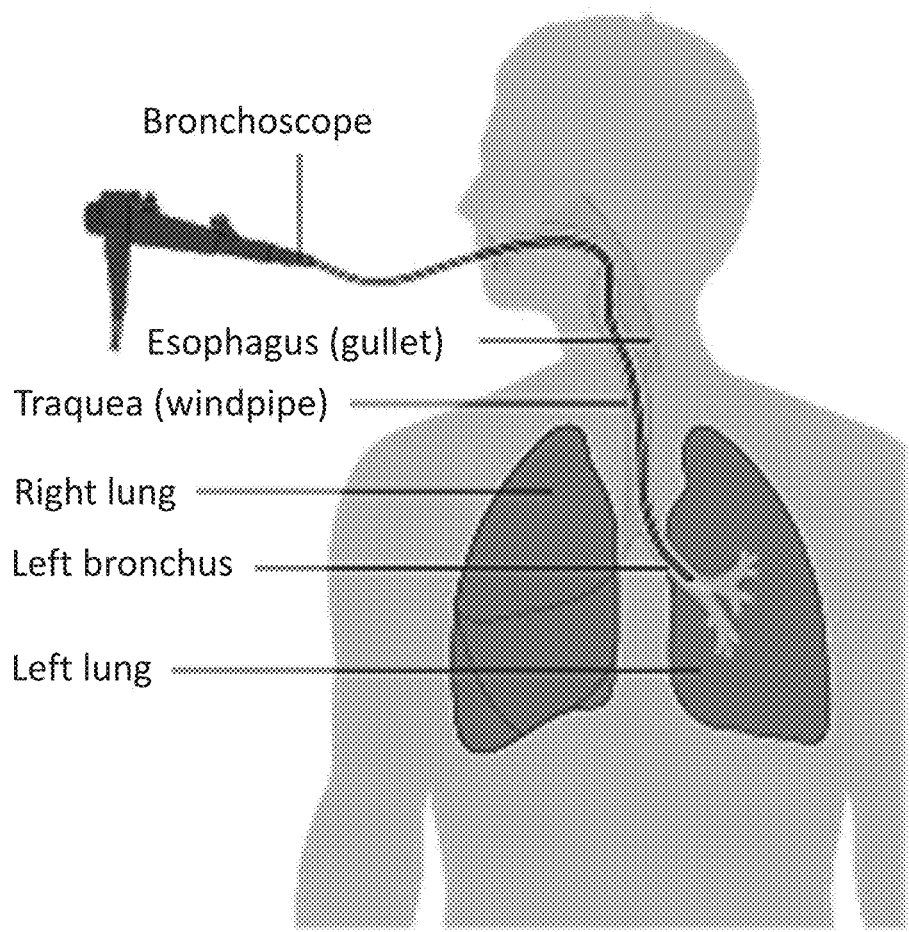
FIG. 3 is a schematic representation of the insertion of a device into the lungs for diagnostic and/or therapeutic purposes, according to some embodiments of the invention.

Inserting the device in to the patient and reaching the desired coordinates 106. In some embodiments, the device is inserted into the patient and the distal end of the device, comprising the ultrasound emitter, is brought close to the location where the treatment is needed, for example a distance of from about 1 mm to about 1 cm from the location; optionally, a distance from about 0.5 mm to about 3 cm from the location; optionally a distance from about 0.1 mm to about 5 cm from the location. FIG. 3 shows a schematic representation of an exemplary bronchoscope brought to a location within the lung. In some embodiments, depending on the diameter of the canal, a diagnostic ultrasonic transducer is inserted. In some embodiments, the diagnostic ultrasonic transducer is activated using, for example, a frequency of about 20 MHz and a 360° field of view.

Figure 4:
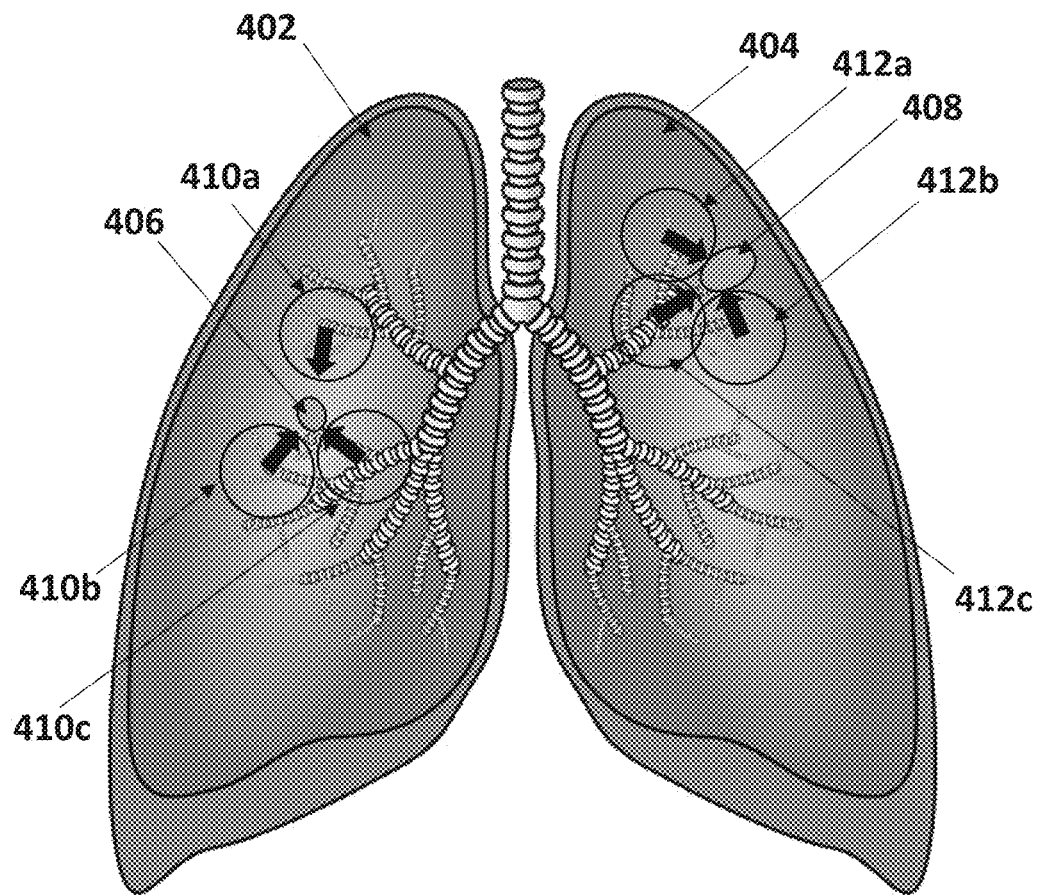
FIG. 4 is a schematic representation of chosen locations from which therapeutic US is performed, according to some embodiments of the invention.

Assessing the parameters of treatment 108. In some embodiments, once the location has been reached, the user assesses the parameters of the treatment, which include one or more of:

1. Choosing one or more, optionally three, locations around the tissue requiring treatment, which are the most echogenic places. FIG. 4, schematically shows the right lung 402 and the left lung 404. There is a small area 406 in need of treatment in the right lung 402, while there is a big area 408 in the left lung 404. FIG. 4 additionally shows three locations 410a, 410b, 410c, which were chosen as the locations from which the treatment will be delivered to the location 406 in the right lung 402; and three locations 412a, 412b, 412c, which were chosen as the locations from which the treatment will be delivered to the location 408 in the right lung 404. The arrows represent the general direction from which the ultrasonic treatment will arrive. In some embodiments, the best echogenic parameters are chosen, for example, as following: based on the CT or X-ray, the user brings a bronchoscope and assesses for one session, from 3 to 5 places that are best visualized by diagnostic ultrasound. In some embodiments, these are places with massive destruction of lung tissue. In some embodiments, therefore, due to their increased echogenicity, these places will be the most optimal places for the insertion and use of the therapeutic US, and it is from those places that the treatment should begin. In some embodiments, if uniformly increased echogenicity is detected in the area of the focus, the user selects the most adjacent lesions and treats them in accordance with the protocol.

In some embodiments, the choice of locations depends, optionally, on the maximum proximity of the transducer to the desired location and optionally, should be a location that is around the desired location.

In some embodiments, optionally, the choice of transducer depends on the location in need of treatment and the diameter of the bronchoscope channel. In some embodiments, the transducer diameter is usually from 2.5 mm to 0.7 mm.

In some embodiments, the treatment plans takes under consideration the depth of the location in need of treatment in relation to the location from which the treatment will be delivered and the size of the location in need of treatment. In some embodiments, the type of the transducer is selected accordingly, for example, localization and size of damage of lung tissue. In some embodiments, radial probe, linear probe or spot probe can be used.

In some embodiments, probes can be both combined, therapeutic US and laser, or only laser or only US. In some embodiments, the size of the probe is selected depending on the location of the tissue required treatment in the lung and, accordingly, the diameter of the bronchoscopy. In some embodiments, the smallest being close to about 2 mm.

In some embodiments, probes can comprise, for example, one or more of the following combinations: laser and ultrasonic in one probe; from one to ten or more therapeutic ultrasound probes in one catheter; laser and ultrasonic separately; laser with an ultrasonic receiver; and ultrasonic diagnostic and ultrasonic therapeutic probes, separated or combined into one probe. In some embodiments, if the treatment is performed only by therapeutic US, the procedure is carried out, for example, twice a day, for five minutes. In some embodiments, in the case of combined laser and ultrasound treatment, they are optionally performed alternately, depending on the condition of the tissue and the patient. In some embodiments, in addition, at certain localizations closer to the mediastinum, it is possible to use the above probes, which are inserted transesophageally or gastroscopically. In some embodiments, in this case, a bronchoscope can be used for transesophageal treatment of tissues in the lungs.

In some embodiments, the treatment profile, meaning the activation of the transducer, is also affected by the location in need of treatment in relation to the location from which the treatment will be delivered and the size of the location in need of treatment. For example, for locations in need of treatment that are located deeper within the tissue, the transducer is activated, for example, at 1 MHz, while in closer locations, the transducer is activated, for example at 3 MHZ.

In some embodiments, the locations from which the treatment will be delivered are selected in different places of the bronchial tree and, optionally, as close as possible to the location in need of treatment. In some embodiments, in each location, which is a part of the bronchial tree having a size, for example, up to 2 cm in size, up to 10 points for the treatment are selected. In some embodiments, each point is processed with forward and backward and/or circular movements for 10 seconds, for example. Therefore, in some embodiments, about 30 points are processed in one session, so the treatment time will constitute 5 min.

In some embodiments, during the treatment session, the temperature is dynamically measured by a thermal sensor. In some embodiments, when the sensed temperature arrives at a certain value, the treatment is either reduced or stopped, and/or an active cooling action is performed, for example, delivering cold liquids to the treatment zone. For example, when the sensed temperature reaches above 41 degrees Celsius, the treatment is either stopped temporarily (until the sensed temperature reaches a certain value) or the delivered ultrasonic force is reduced. In some embodiments, for example, cold liquids are delivered using a separate broncho/endoscope channel, optionally automatically, when a certain temperature value is sensed. In some embodiments, a potential advantage of actively monitoring the temperature is that it allows to actively and specifically control the temperature, as explained above, which is important, on one side, for the success of the treatment, and on the other side, for the safety of the patient.

Providing treatment 110. In some embodiments, once the treatment plan is ready, the catheter with diagnostic ultrasonic transducer is taken out from bronchoscope and is replaced with a treatment ultrasonic transducer. In some embodiments, ultrasonic or laser treatment devices are inserted intrabronchially and according to the localization of the tissue requiring treatment, the devices are brought so that the probe is located as close as possible to the desired location.

In some embodiments, treatment sessions comprise one or more of the following parameters:
  Frequency of treatment: In some embodiments, the treatment sessions are carried out once a day, optionally twice a day, optionally several times a day. In some embodiments, the treatment sessions are carried out every day, optionally every other day, optionally at any intervals chosen by the medical personnel.

In some embodiments, depending on the size of the lesion, during the first seven to ten days of treatment, chosen locations from which treatment is delivered are alternated. In some embodiments, a potential advantage of alternating locations from which treatment is delivered is that it allows to treat the locations from different sides, while allowing the death process of the tissues to occur in those previous treated locations. Another potential advantage is that it allows to treat the maximum area possible. In some embodiments, during the first seven to ten days of treatment, the area to be treated is treated at least 3 times from each chosen location.

In some embodiments, the US beam is not uniform and changes in its nature with distance from the transducer. In some embodiments, the US beam nearest to the treatment head is called the NEAR field, the INTERFERENCE field or the Fresnel zone. In some embodiments, the behavior of the US in this field is far from regular, with areas of significant interference. In some embodiments, the size (length) of the near field can be calculated using r2/l where r=the radius of the transducer crystal and l=the US wavelength according to the frequency being used (for example 0.5 mm for 3 MHz and 1.5 mm for 1.0 MHZ).

Assessing whether to repeat or stop treatment 112. In some embodiments, after seven to ten days of treatment, a new CT scan is performed for comparison. In some embodiments, in case of the medical personnel arrives at the conclusion that there are positive clinical results, optionally based on the imaging results, treatment can be stopped after three weeks. In some embodiments, during the rehabilitation period, which begins immediately after the patient exits the critical condition and lasts until the restoration of respiratory function. In some embodiments, treatment is performed, for example, once or twice a week. It should be noted that fibrotic changes in the lungs after ARDS are very severe and strongly affect respiratory function. However, in about 40% of patients they are eventually replaced by normal lung tissue. In some embodiments, the rehabilitation period can be, for example, up to 6 months, or until complete removal of scars in the treatment location in the lungs.

In some embodiments, in case of the medical personnel arrives at the conclusion that there are no positive clinical results, optionally based on the imaging results, after 7 to 10 days, the treatment is stopped and treatment is then given to the different lung or a different spot in the same lung, depending on existing echogenic zones opportunities.

In some embodiments, in the case where laser is used together with the US treatment, the exposure time is distributed, for example, ⅔ exposure to US and ⅓ exposure to laser. In this case, a catheter with a laser probe is inserted instead of a catheter with a therapeutic ultrasound probe.

In some embodiments, the same principals apply also for treating other maladies, for example, when treating pulmonary embolism or other mediastinal vascular complications, or when treating transesophageally with therapeutic ultrasound.

In some embodiments, the same principals apply for treatment with topical medicinal agents that, through ultrasound, penetrate the affected areas of the lungs.

In some embodiments, during treatment, or more pharmaceutical are provided to the patient, for example anti-inflammatory drugs, anti-coagulants, etc.

Figure 6:
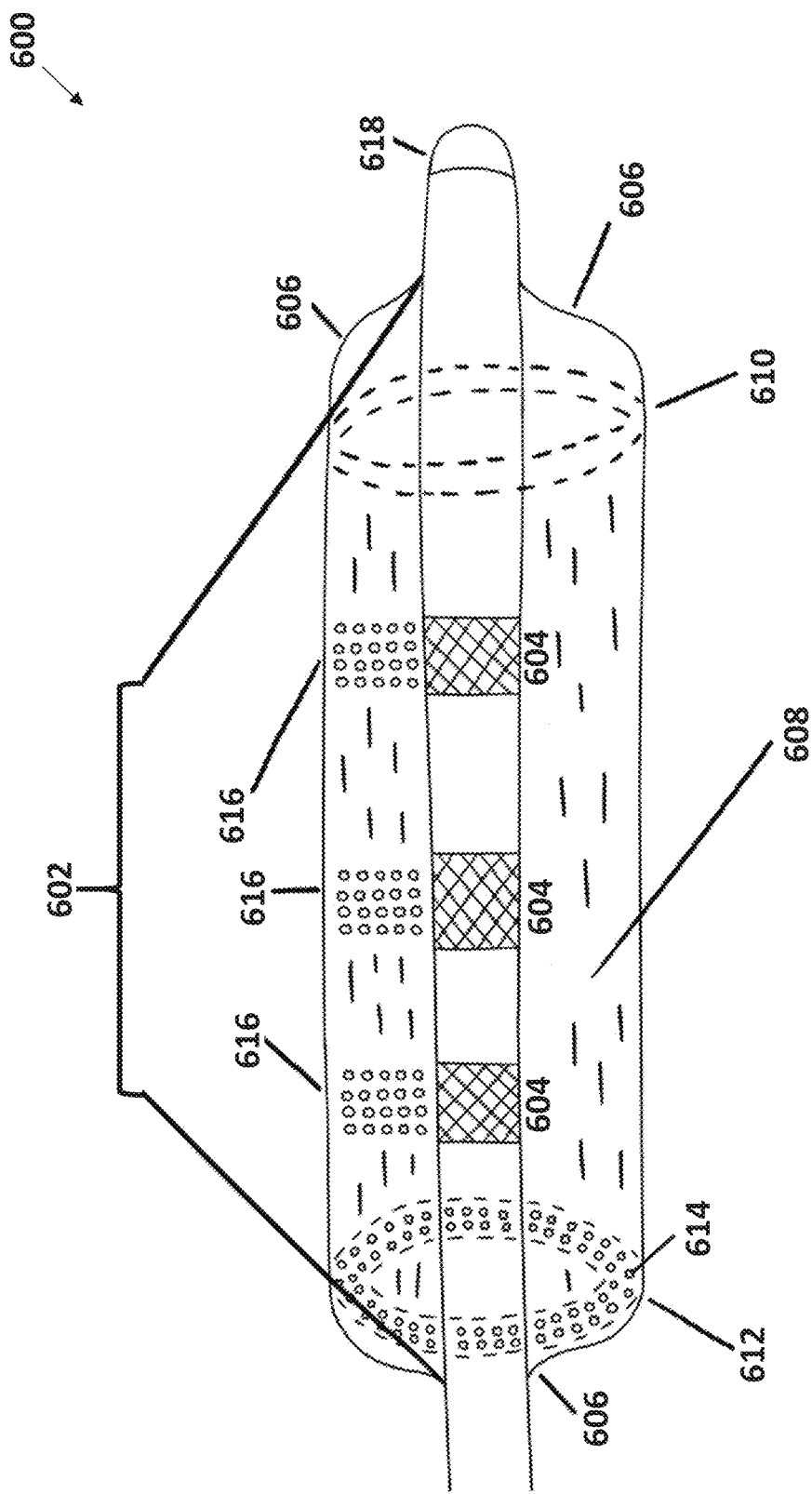
FIG. 6 is a schematic representation of an exemplary calibrating/treating Catheter (CTCat) 600, according to some embodiments of the invention.

Referring now to FIG. 6, showing a schematic representation of an exemplary calibrating/treating Catheter (CTCat) 600, according to some embodiments of the invention.

In some embodiments, the CTCat is a catheter comprising a dedicated distal end 602 configured to allow performing both calibration and treatment. In some embodiments, a potential advantage of the CTCat is that it potentially avoids the need to perform a two-step procedure, one of locating the proper location for providing the treatment and another to bring the device that actually provides the treatment. In some embodiments, two distinct devices are used, one for the calibration and one treatment.

In some embodiments, the distal end 602 comprises one or more ultrasonic transducers 604. In some embodiments, the distal end 602 is covered by a balloon 606. In some embodiments, the balloon 606 can be inflated with a liquid 608, for example saline and/or a drug or medicine. In some embodiments, the balloon 606 comprises a first electrode 610 located at a distal part of the balloon 606, and a second electrode 612 located a proximal part of the balloon 606. In some embodiments, at the area of the second electrode 612, the balloon 606 comprises a plurality of orifices 614 configured to be actuated when performing iontophoresis treatment (see below). In some embodiments, the location of the first electrode 610 and the second electrode 612 are set so the location of the first electrode 610 is distally to the location of the transducer 604 that is most distal between all the possible transducers, while the second electrode 612 is proximally to the location of the transducer 604 that is most proximal between all the possible transducers. In other words, all possible transducers 604 are located between the first electrode 610 and the second electrode 612. In some embodiments, optionally, the balloon 606 further comprises additional orifices 616 configured to be actuated when performing phonophoresis treatment (see below), and located at positions matching the positions of the transducers 604. In some embodiments, optionally, the distal end 602 comprises a video camera 618 configured to assist the user when navigating the CTCat 600 within the patient.

In some embodiments, CTCat 600 have a size range, depending on their resistance, and differ between each other in their Contact Pressure (i.e.: minimum pressure to be created in the balloon to achieve full contact with the bronchial wall and the perforation holes remain closed). In some embodiments, a potential advantage of using contact pressure is that it potentially prevents overgrowth and/or bronchial wall ischemia, which are frequent complications from excessive inflating of the balloon. In some embodiments, for example, a catheter with resistance R1 has a contact pressure of 10 mmH2O, a catheter with a resistance R2 has a contact pressure of 15 mmH2O, and a catheter with a resistance R3 has a contact pressure of 20 mmH2O, and so on.

Exemplary Methods When Using an Exemplary CTCat

Figure 7:
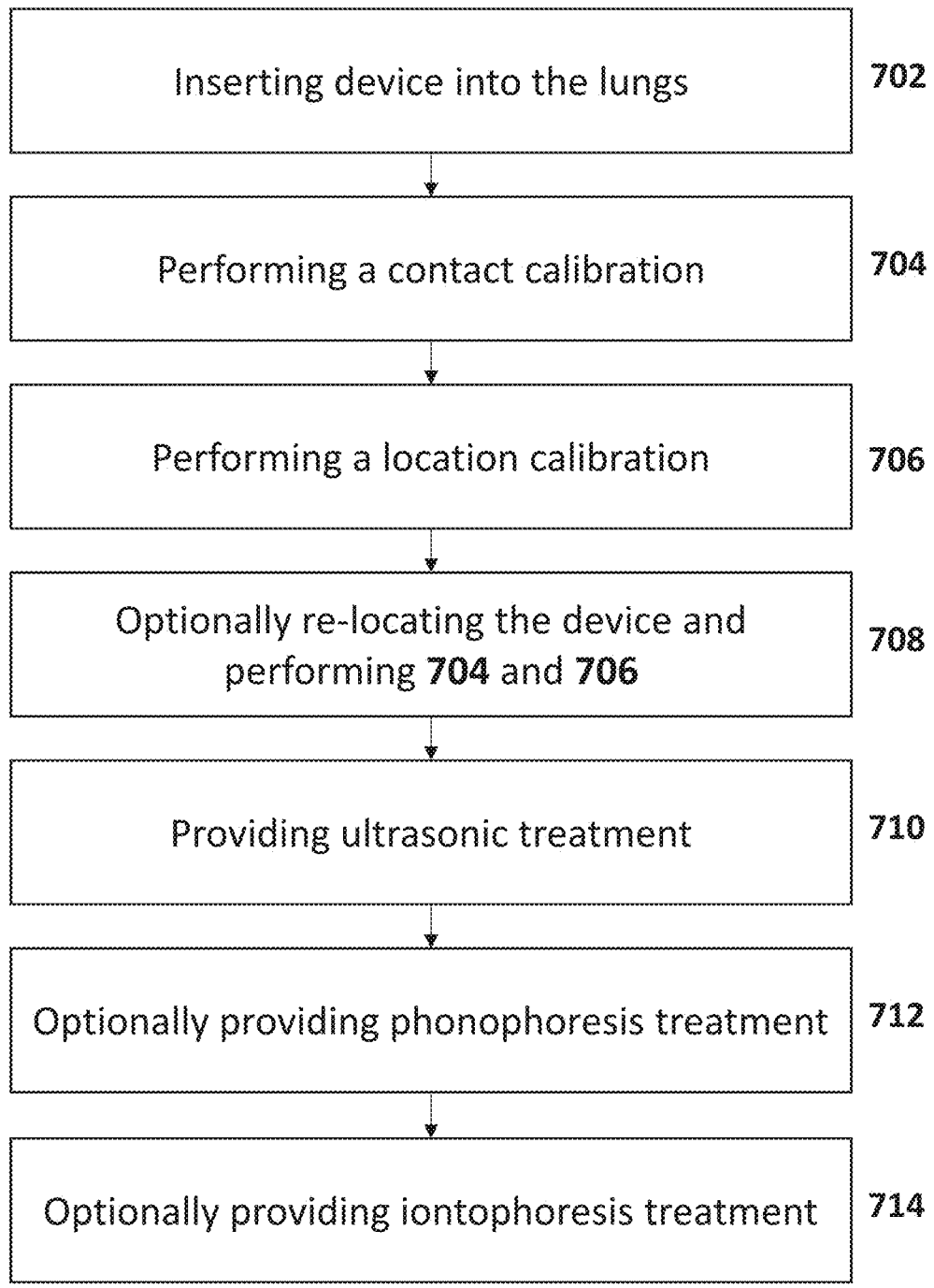
FIG. 7 is a flowchart of an exemplary general method of use of a CTCat, according to some embodiments of the invention.

Referring now to FIG. 7, showing a flowchart of an exemplary general method of use of a CTCat, according to some embodiments of the invention.

In the following paragraph a general overview of the method will be explained, then followed by more detail description of the specific actions.

In some embodiments, the method comprises inserting the CTCat into the patient, optionally using the video camera 618, (702). In some embodiments, the insertion is performed for example via the esophagus and/or via the trachea.

In some embodiments, the method comprises performing a contact calibration (704).

In some embodiments, the method comprises performing a location calibration (706).

In some embodiments, optionally, the method comprises relocating the CTCat device to a new location and performing again actions 704 and 706 (708). In some embodiments, a reason to re-locate the CTCat is that either the contact calibration has failed or the location calibration has failed.

In some embodiments, the method comprises providing ultrasonic treatment (710).

In some embodiments, the method comprises optionally providing phonophoresis treatment (712).

In some embodiments, the method comprises optionally providing iontophoresis treatment (714).

Exemplary Method of Contact Calibration 704

Figure 8:
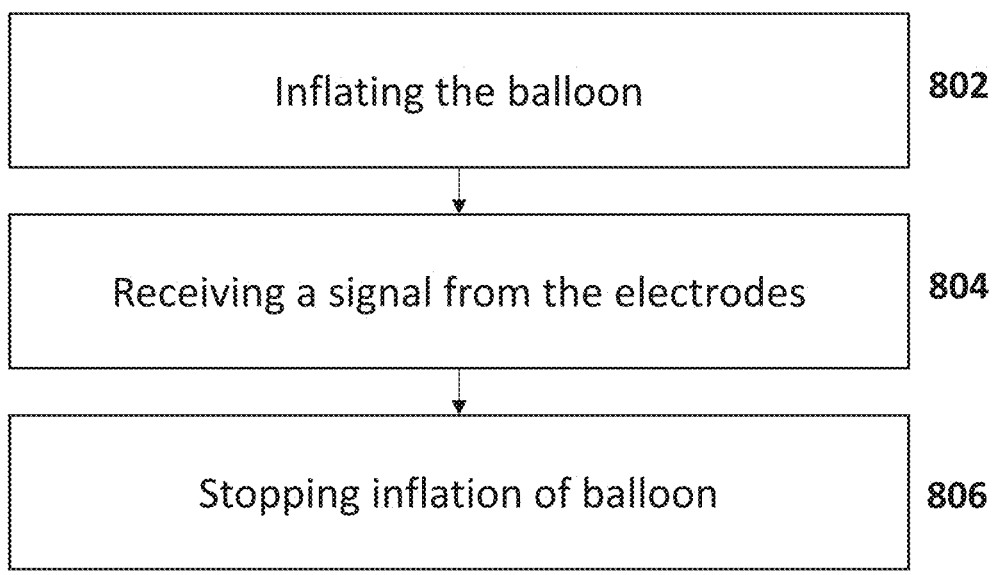
FIG. 8 is a flowchart of an exemplary contact calibration method, according to some embodiments of the invention.

Referring now to FIG. 8, showing a flowchart of an exemplary contact calibration method, according to some embodiments of the invention. In some embodiments, once the CTCat is brought to a potential location (optionally chosen according to X-ray images and/or CT images), a contact calibration is performed.

In some embodiments, contact calibration is performed to ensure that the ultrasonic waves will pass the bronchial walls by ensuring that the distal end of the device is actually in continuous contact with the bronchial walls.

In some embodiments, the contact calibration is performed by inflating the balloon, optionally slowly inflating the balloon (802), until both the first electrode and the second electrode are in contact with the bronchial walls. In some embodiments, bringing both the first electrode and the second electrode in contact with the bronchial walls will cause the closure of the circuit between the first electrode and the second electrode, which will cause sending a signal to the user (therefore the user will receive the signal 804) that the circuit has been closed. In some embodiments, the user then sops inflating the balloon 806.

In some embodiments, this method provides the minimum pressure required to inflate the balloon for a maximum contact with the bronchial walls—referred hereinafter as Contact Pressure or Pcont. In some embodiments, at the Pcont the balloon is in contact with the bronchial walls without overstretching them and without causing ischemia of the tissue (or other complications).

In some embodiments, at the Pcont the balloon is in contact with the bronchial walls without opening neither orifices 616 (used in Phonophoresis treatment) nor orifices 614 (used for iontophoresis treatment).

Exemplary Location Calibration 706

Figure 9:
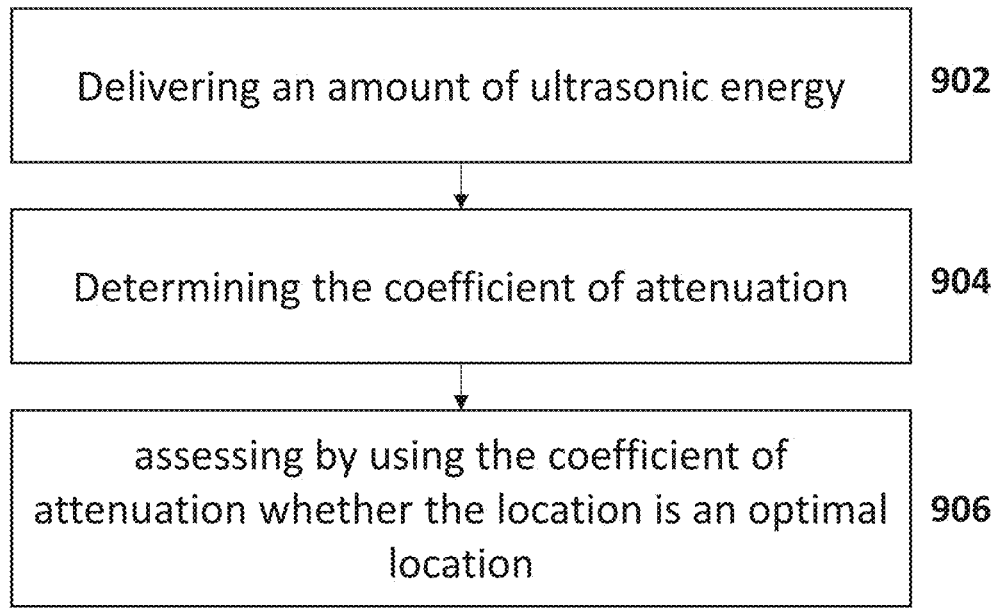
FIG. 9 is a flowchart of an exemplary location calibration method, according to some embodiments of the invention.

Referring now to FIG. 9, showing a flowchart of an exemplary location calibration method, according to some embodiments of the invention. In some embodiments, the location calibration is performed to assess the optimal location to position the CTCat device, in relation to the location requiring treatment, for delivering the treatment. In some embodiments, the optimal location is characterized by being location where there is no air between the distal end of the device and the location requiring treatment. In some embodiments, the optimal location is characterized by being a location closest to the location requiring treatment. In some embodiments, the optimal location is characterized by being both a location where there is no air between the probe and the location requiring treatment and it is the location closest to the location requiring treatment. In some embodiments, the calibration process utilizes attenuation of the delivered ultrasonic energy to select the location where the probe will be positioned.

Without being bound to theory, attenuation is the result of several features of sound wave interaction with tissue and tissue boundaries, including for example: reflection, refraction, scatter, absorption, interference. Conversion of transmitted energy to another form of energy, such as heat (absorption), is the primary mean by which attenuation of ultrasound occurs in biologic tissue, with scatter comprising the other significant contributing factor. The intrinsic propensity of a medium (for example a tissue) to attenuate sound waves at a given frequency may be represented by its attenuation coefficient (represented by the Greek letter alpha ($\alpha$), and measured in dB/[mHz×cm]). The following are examples of the attenuation coefficients and properties of some commonly encountered tissues, which are brought just as examples to allow a person having skills in the art to understand the invention:

Highest Attenuation Coefficients
   Aerated lung ($\alpha > 34.0$) presents a virtually impermeable barrier to ultrasound, as does cortical bone ($\alpha \sim 20.0$)
   Loss of lung aeration will alter the degree to which it attenuates ultrasound waves Lowest Attenuation Coefficients
   Water and blood attenuate ultrasound waves to a hardly appreciable degree ($\alpha \sim 0.18$)
   Other soft tissues, such as organs or skeletal muscle, have attenuation coefficients which lie between these extremes.

Thus, by determining the coefficient of attenuation, we can not only understand the possibility of patency of the lung tissue for ultrasound, but also it allows using the value of the coefficient for assuming what processes will occur in the treatment area at the tissue level and, accordingly, correlate the composition and dose of the drugs used (when drugs are needed).

Therefore, in some embodiments, the location calibration comprises:
   a. delivering an amount of ultrasonic energy (902);
   b. determining the coefficient of attenuation (904);
   c. assessing by using the coefficient of attenuation whether the location is an optimal location (906).

In some embodiments, optionally other indicators can be used for calibration, for example, X-rays, CT scans, etc.

Exemplary Ultrasonic Treatment

In some embodiments, as mentioned above, the treatment profile, meaning the activation of the transducer, is affected by the location in need of treatment in relation to the location from which the treatment will be delivered and the size of the location in need of treatment. For example, for locations in need of treatment that are located deeper within the tissue, the transducer is activated, for example, at 1 MHZ, while in closer locations, the transducer is activated, for example at 3 MHZ.

In some embodiments, treatment sessions comprise one or more of the following parameters:
   Frequency of treatment: In some embodiments, the treatment sessions are carried out once a day, optionally twice a day, optionally several times a day. In some embodiments, the treatment sessions are carried out every day, optionally every other day, optionally at any intervals chosen by the medical personnel.
   In some embodiments, depending on the size of the lesion, during the first seven to ten days of treatment, chosen locations from which treatment is delivered are alternated. In some embodiments, a potential advantage of alternating locations from which treatment is delivered is that it allows to treat the locations from different sides, while allowing the death process of the tissues to occur in those previous treated locations. Another potential advantage is that it allows to treat the maximum area possible. In some embodiments, during the first seven to ten days of treatment, the area to be treated is treated at least 3 times from each chosen location.

In some embodiments, the US beam is not uniform and changes in its nature with distance from the transducer. In some embodiments, the US beam nearest to the treatment head is called the NEAR field, the INTERFERENCE field or the Fresnel zone. In some embodiments, the behavior of the US in this field is far from regular, with areas of significant interference. In some embodiments, the size (length) of the near field can be calculated using r2/l where r=the radius of the transducer crystal and l=the US wavelength according to the frequency being used (for example 0.5 mm for 3 MHz and 1.5 mm for 1.0 MHZ).

In some embodiments, providing ultrasonic treatment comprises providing ultrasonic treatment with interferential current. In some embodiments, two medium frequency currents are used. In some embodiments, the frequency currents act as carrier waves and they do not produce muscle or nerve stimulation. In some embodiments, the frequency currents are used to get the greater depth of penetration and/or to produce interferential current.

Figure 5:
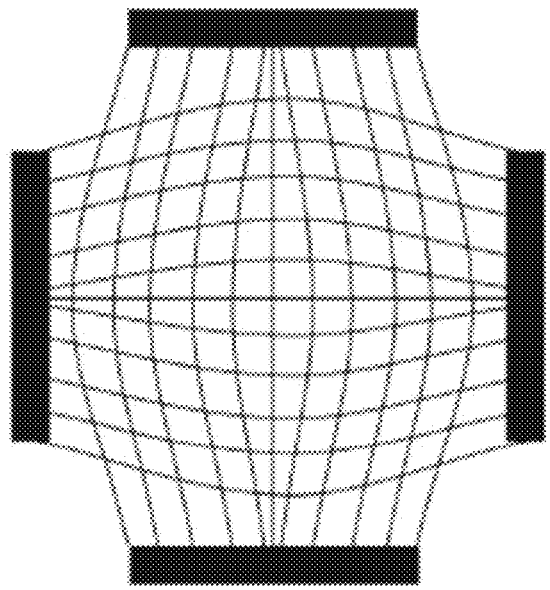
FIG. 5 is a schematic representation of an interference electric field generated by two CTCat, according to some embodiments of the invention.
Figure 5:
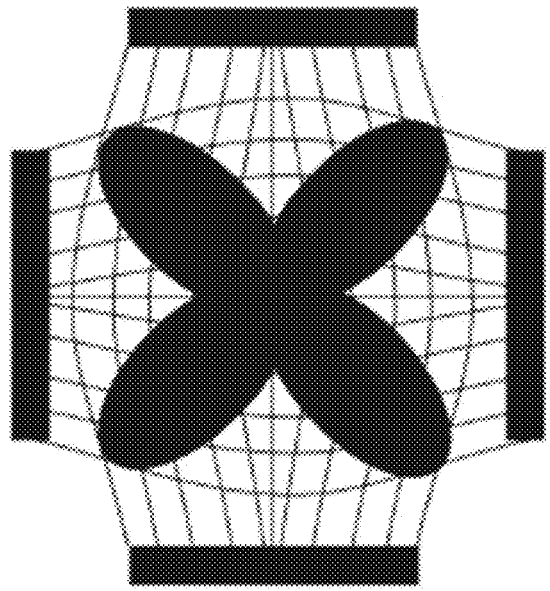
Figure 10:
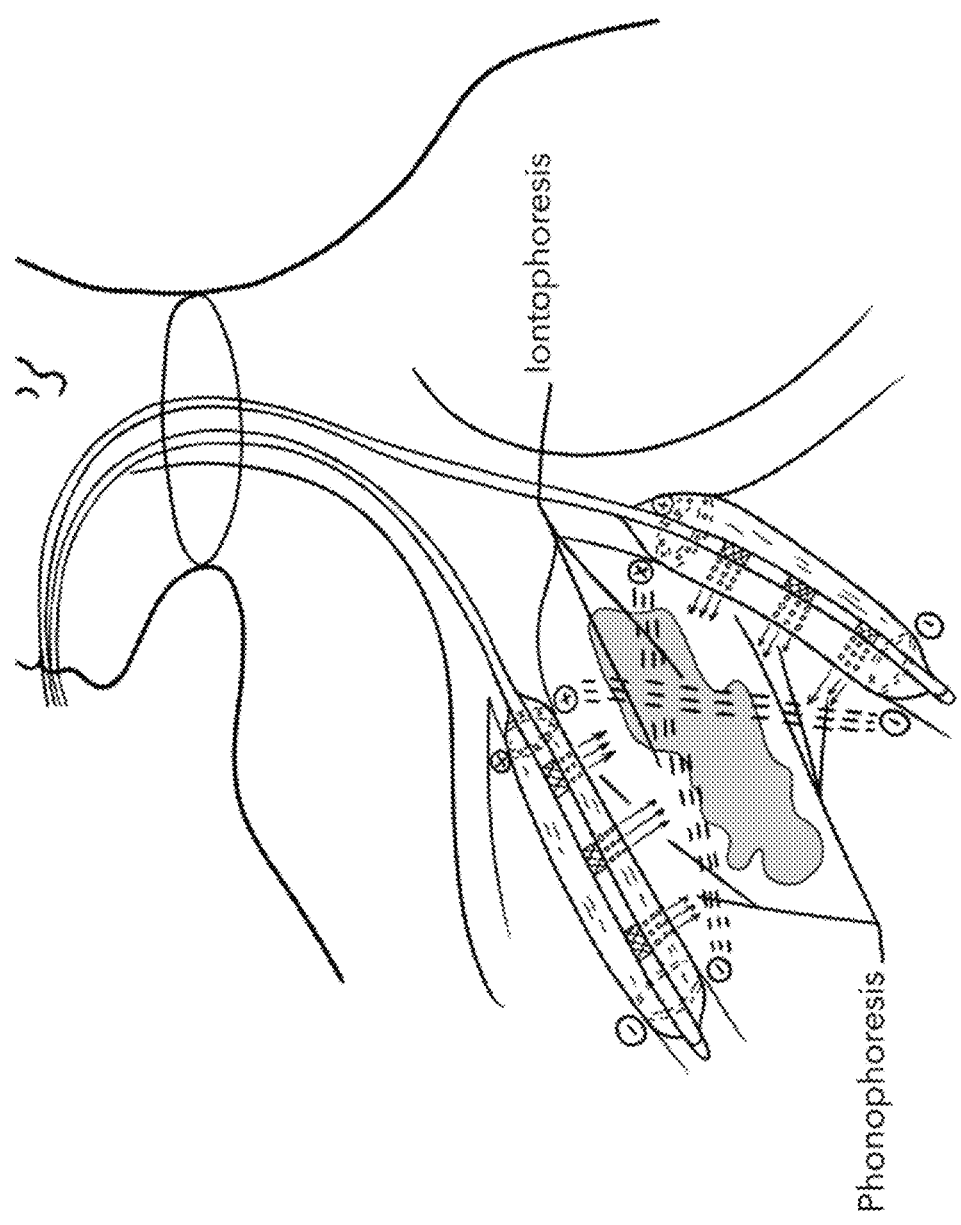
FIG. 10 is a schematic representation of an exemplary generation of an interferential current by two CTCat, according to some embodiments of the invention.

Referring now to FIG. 5, showing a schematic representation of an interference electric field generated by two CTCat, according to some embodiments of the invention. In some embodiments, as stated above, an interference electric field is used during the treatment. In some embodiments, in order to produce the interferential current, two medium frequency currents are used. For example, Current A: f1—this current is set on the machine, thus called "intrinsic/carrier frequency", for example at 4000 Hz (2000 Hz and 6000 Hz also available); then, Current B: f2—same amplitude, but slightly higher frequency; set by the user. In some embodiments, for example, f2 would be variable from 4001 Hz to 4150 Hz. In some embodiments, f2 will move within a range of frequencies. In some embodiments, a potential advantage of doing this is that it potentially limits accommodation and habituation to current. In some embodiments, F=f2−f1, where the amplitude of F (Current C) is not constant. In some embodiments, this is called as beat frequency current C. In some embodiments, F=f2−f1 ranges from 1 Hz to 150 Hz (the frequency swing is also referred to as spectrum or sweep). In some embodiments, the area in which interferential current is set-up remains stationary. In some embodiments, this area of static interference gives an appearance of clover leaf (as shown in FIG. 10) as a result of vector addition of two currents and it lies at a 45° angle to the perpendicular lines from each electrode. In some embodiments, during treatment, 1, 2, 3, 4 or more electrodes are used.

In some embodiments, the field is used for one or more of:
1. For determining the Contact Pressure, i.e. the minimum pressure at which there will be full contact between balloon and the bronchial wall, which is important for ultrasound treatment. In some embodiments, the Contact Pressure allows to control the pressure in the balloon and avoid injury and ischemia of the bronchial mucosa, which can be in case of excessive pressure. In some embodiments, the same principle can be applied to all types of catheters at any location.
2. For performing Iontophoresis (see below), during which a drug is introduced deep into the tissues as a means of local drug application. In some embodiments, by inflating the balloon to the pressure levels described below, that is, to Pion (pressure for iontophoresis), openings are opened in the proximal electrode and, through Iontophoresis, drugs are introduced into the lung wound. In some embodiments, a potential advantage of having the ability to provide iontophoresis treatment is that where in cases where calibration cannot identify quality-accessible sites for ultrasound treatment, iontophoresis can be used alone as treatment.

Referring now to FIG. 10, showing a schematic representation of an exemplary generation of an interferential current by two CTCat, according to some embodiments of the invention. In some embodiments, when obtaining interferential current, for example, 4 fabric electrodes are fixed to the pair of catheters, to the end of each balloon. In some embodiments, if at the distal end of the balloon there is the positive charge, then at the proximal end of second balloon there will be a negative charge. In some embodiments, electrodes are ring-shaped and installed in the outer part of the balloons, as explained above, at its two ends.

Assessing whether to repeat or stop treatment. In some embodiments, after seven to ten days of treatment, a new CT scan is performed for comparison. In some embodiments, in case of the medical personnel arrives at the conclusion that there are positive clinical results, optionally based on the imaging results, treatment can be stopped after three weeks. In some embodiments, during the rehabilitation period, which begins immediately after the patient exits the critical condition and lasts until the restoration of respiratory function. In some embodiments, treatment is performed, for example, once or twice a week. It should be noted that fibrotic changes in the lungs after ARDS are very severe and strongly affect respiratory function. However, in about 40% of patients they are eventually replaced by normal lung tissue. In some embodiments, the rehabilitation period can be, for example, up to 6 months, or until complete removal of scars in the treatment location in the lungs.

Exemplary Provision of Therapeutic Agents During Treatment

In some embodiments, the treatment optionally comprises locally providing one or more pharmaceuticals/drugs during the treatment. In some embodiments, as explained above, the ultrasonic treatment is provided by using the CTCat with transducers covered with the balloon in which there are micro-holes in front of the transducers that open under a certain pressure within the balloon. In some embodiments, the micro-holes allow the passage of the pharmaceuticals/drugs through them. In some embodiments, this is performed while providing ultrasonic treatment. In some embodiments, the ultrasonic wave mechanically introduces the pharmaceuticals/drugs into the adjacent tissues and promotes their delivery into the lesion (see below—phonophoresis treatment).

Exemplary Phonophoresis Treatment

In some embodiments, optionally, in addition of providing ultrasonic treatment, a phonophoresis treatment is provided. In some embodiments, in addition or alternatively to saline, a drug/medicine is provided within the liquid that inflates the balloon. In some embodiments, the ultrasonic treatment is used to deliver the drugs into the tissue using the phonophoresis principle. In some embodiments, when providing phonophoresis treatment, the balloon is further inflated in order to open the orifices 616, located at the zone of the transducers 604. For example, at Pcont (found during the contact calibration), a quantity of 20 mmH2O was found to be the quantity required to reach Pcont. Then, for example, an additional 5 mmH2O (a total of 25 mmH2O within the balloon) are inserted into the balloon in order to open only the orifices 616 located at the zone of the transducers 604 (without opening the orifices 614 located at the area of the second electrode 612). In some embodiments, this pressure is referred hereinafter as Pressure Phonophoresis or Pphon—therefore Pphon=Pcon+5 mmH2O.

Exemplary Iontophoresis Treatment

In some embodiments, optionally, in addition of providing ultrasonic treatment and/or phonophoresis treatment, an iontophoresis treatment is provided. In some embodiments, in addition or alternatively to saline, a drug/medicine is provided within the liquid that inflates the balloon. In some embodiments, the iontophoresis treatment is used to deliver the drugs into the tissue by interferential electrical field. In some embodiments, when providing iontophoresis treatment, the balloon is further inflated in order to open the orifices 614, located at the zone of the second electrode 612. For example, at Pcont (found during the contact calibration), a quantity of 20 mmH2O was found to be the quantity required to reach Pcont. Then, for example, an additional 5 mmH2O (a total of 25 mmH2O within the balloon) are inserted into the balloon in order to open only the orifices 616 located at the zone of the transducers 604 (without opening the orifices 614 located at the area of the second electrode 612), achieving Pphon. Then, additionally, another additional 5 mmH2O (a total of 30 mmH2O within the balloon) are inserted into the balloon in order to additionally open orifices 614, located at the zone of the second electrode 612. In some embodiments, this pressure is referred hereinafter as Pressure Iontophoresis or Pion—therefore Pion=Pcon+Pphon+5 mmH2O. Therefore, by inflating the balloon to 10 mm H20, the openings in the proximal electrode of the balloon are opened, with corresponding polarity of the injected substance within the liquid and the iontophoresis, the process begins.

In some embodiments, when performing iontophoresis, an electric field is used as a drug promoter. Without being bound to theory, iontophoresis allows the movement of the drugs by using the drug ions, depending on their charge, to move the drug into the tissue. It is based on the principle that in a given electric field, positively charged drug ions (cations) are repelled by a positive electrode (anode) and are directed to the cathode. For example, Ketoprofen being repelled by the negative electrode (cathode), follow the anode. In some embodiments, interferential current is used for iontophoresis.

Exemplary Catheter System

Figure 11:
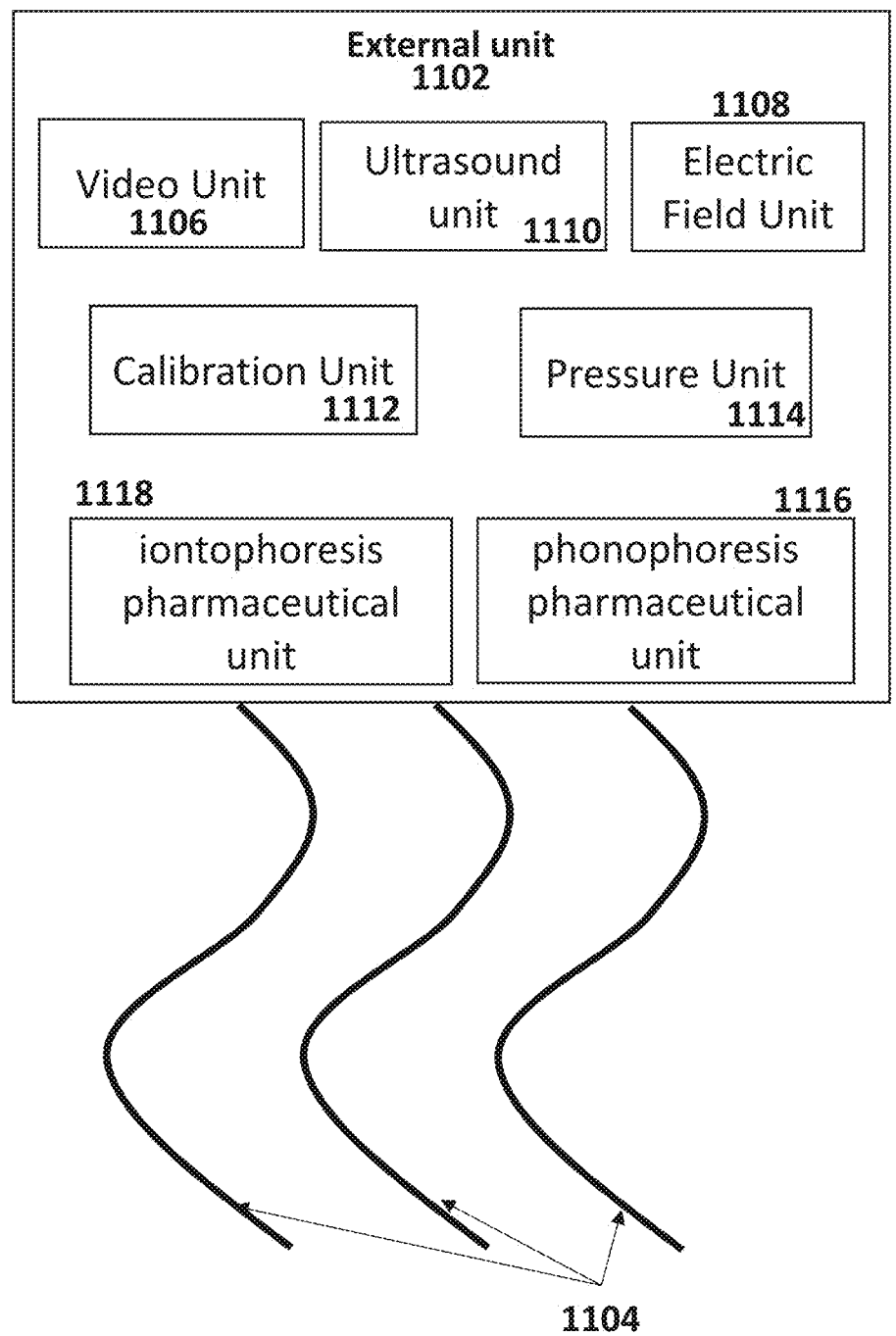
FIG. 11 is a schematic representation of a catheter system, according to some embodiments of the invention.

Referring now to FIG. 11, showing a schematic representation of an exemplary catheter system according to some embodiments of the invention. In some embodiments, the system comprises at least one CTCat. Optionally, the system comprises more than one CTCat, for example two, three, four or more CTCats.

In some embodiments, all the CTCats 1104 are connected to a centralized external unit 1102 comprising all the required hardware for the operation of the CTCats.

In some embodiments, the external unit comprises one or more of the following:

a. a video unit 1106 comprising a navigation system, configured for manipulating said at least one catheter and provide visualization means from said video camera to a user;
b. an electric field unit 1108 configured for generating an interference field; In some embodiments, the electric field unit is configured to provide current to a first catheter at a first frequency and to provide current to a second catheter at a second frequency. In some embodiments, first frequency is of about 4000 Hz and said second frequency is from about 4100 Hz to about 4500 Hz. In some embodiments, the electric field unit is configured to provide electrical current which does not exceed 13 milliamps.
c. an ultrasonic unit 1110 configured to generate ultrasonic waves from about 0.5 MHZ to about 3 MHz, with a power up to 2 watts per $cm^2$;
d. a calibration unit 1112 configured for specifying a attenuation coefficient in different locations and further configured for determining the optimal localization of said one or more ultrasonic transmitters;
e. a pressure unit 1114 configured for maintaining and monitoring a pressure in said balloon;
f. a phonophoresis pharmaceutical unit 1116 configured for monitoring and administering said at least one drug during phonophoresis treatment;
g. a iontophoresis pharmaceutical unit 1118 configured for monitoring and administering said at least one drug during iontophoresis treatment.

Exemplary Additional Information

In some embodiments, a balloon might be characterized by having different values of Pcont, Pphon and Pion. In some embodiments, a maximum quantity of liquid that can be inserted in a balloon is from about 20 mmH2O to about 40 mmH2O, optionally from about 15 mmH2O to about 50 mmH2O, optionally more than 50 mmH2O.

In some embodiments, CTCat differ in resistance and polarity. In some embodiments, different people have different resistance of the broncho-alviolar tree, therefore, there are CTCat with different balloon resistance, so as not to cause mechanical damage to the walls of the broncho-alviolar tree.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A catheter system for treating a wound, comprising:
   a. at least one catheter comprising proximal end and a distal end; said distal end comprising:
      i. one or more ultrasonic transmitters;
      ii. an inflatable balloon covering said one or more ultrasonic transmitters; said inflatable balloon comprising a first electrode located at a proximal location of said inflatable balloon and a second electrode located at a distal location of said inflatable balloon;
      iii. a plurality of a first type of openings located on a surface of said balloon; said location of said first type of openings being co-located to a location of said one or more ultrasonic transmitters on said catheter;
      iv. a plurality of a second type of openings located on a surface of said balloon; said location of said second type of openings being co-located to a location of said first electrode.

2. The catheter system according to claim 1, further comprising at least one liquid configured to inflate said inflatable balloon.

3. The catheter system according to claim 2, wherein said at least one liquid comprises at least one drug.

4. The catheter system according to claim 2, wherein said at least one liquid is saline.

5. The catheter system according to claim 1, further comprising one or more controls located at said proximal end of said catheter device and configured to control a movement of said distal end of said catheter device.

6. The catheter system according to claim 1, further comprising a video camera located at most distal end of said catheter device.

7. The catheter system according to claim 1, wherein said at least one catheter is configured to provide phonophoresis treatment.

8. The catheter system according to claim 1, wherein said at least one catheter is configured to provide iontophoresis treatment.

9. The catheter system according to claim 1, further comprising an external unit to which said at least one catheter is connected, said external unit comprising:
   a. a video unit comprising a navigation system, configured for manipulating said at least one catheter and provide visualization means from said video camera to a user;
   b. an electric field unit configured for generating an interference field;
   c. an ultrasonic unit configured to generate ultrasonic waves from about 0.5 MHZ to about 3 MHz, with a power up to 2 watts per $cm^2$;
   d. a calibration unit configured for specifying a attenuation coefficient in different locations and further configured for determining the optimal localization of said one or more ultrasonic transmitters;
   e. a pressure unit configured for maintaining and monitoring a pressure in said balloon;
   f. a phonophoresis pharmaceutical unit configured for monitoring and administering said at least one drug during phonophoresis treatment;
   g. a iontophoresis pharmaceutical unit configured for monitoring and administering said at least one drug during iontophoresis treatment.

10. The catheter system according to claim 9, wherein said electric field unit is configured to provide current to a first catheter at a first frequency and to provide current to a second catheter at a second frequency.

11. The catheter system according to claim 10, wherein said first frequency is of about 4000 Hz and said second frequency is from about 4100 Hz to about 4500 Hz.

12. The catheter system according to claim 9, wherein said electric field unit is configured to provide electrical current which does not exceed 13 milliamps.

* * * * *